(12) United States Patent
Zhang et al.

(10) Patent No.: US 12,383,752 B2
(45) Date of Patent: Aug. 12, 2025

(54) METHOD AND APPARATUS FOR DISCRIMINATING TACHYCARDIA EVENTS IN A MEDICAL DEVICE

(71) Applicant: Medtronic, Inc., Minneapolis, MN (US)

(72) Inventors: Xusheng Zhang, Shoreview, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 141 days.

(21) Appl. No.: 18/182,795

(22) Filed: Mar. 13, 2023

(65) Prior Publication Data

US 2023/0285765 A1 Sep. 14, 2023

Related U.S. Application Data

(60) Division of application No. 16/537,969, filed on Aug. 12, 2019, now Pat. No. 11,602,639, which is a (Continued)

(51) Int. Cl.
*A61N 1/38* (2006.01)
*A61N 1/39* (2006.01)

(52) U.S. Cl.
CPC .................. *A61N 1/3925* (2013.01)

(58) Field of Classification Search
CPC .................... A61N 1/3956; A61N 1/37512
See application file for complete search history.

(56) References Cited

U.S. PATENT DOCUMENTS 4,374,382 A 2/1983 Markowitz
4,548,209 A 10/1985 Wielders et al.
(Continued)

FOREIGN PATENT DOCUMENTS

AU 20100201351 4/2010
CN 1662279 A 8/2005
(Continued)

OTHER PUBLICATIONS

C00007180.WOU2 (PCT/US2015/025152) PCT Notification of Transmittal of the International Search Report and the Written Opinion of the International Searching Authority, Mailed Jun. 18, 2015, 9 pp.
(Continued)

*Primary Examiner* — Michael J D'Abreu
(74) *Attorney, Agent, or Firm* — Shumaker & Sieffert, P.A.

(57) ABSTRACT

A method and medical device for detecting a cardiac event that includes sensing cardiac signals from a plurality of electrodes, the plurality of electrodes forming a first sensing vector and a second sensing vector, identifying the cardiac event as one of a shockable event and a non-shockable event in response to first processing of a first interval sensed along the first sensing vector during a predetermined sensing window and a second interval simultaneously sensed along the second sensing vector, performing second processing of the first interval and the second interval, different from the first processing, in response to the cardiac event being identified as a shockable event, and determining whether to delay identifying the cardiac event being shockable in response to the second processing of the first interval and the second interval.

20 Claims, 13 Drawing Sheets

Related U.S. Application Data continuation of application No. 14/242,391, filed on Apr. 1, 2014, now Pat. No. 10,376,705.

(56) References Cited

U.S. PATENT DOCUMENTS

| | | |
|---|---|---|
| 4,556,063 A | 12/1985 | Thompson et al. |
| 4,567,892 A | 2/1986 | Plicchi et al. |
| 4,870,974 A | 10/1989 | Wang |
| 5,127,404 A | 7/1992 | Wybomy et al. |
| 5,163,427 A | 11/1992 | Keimel |
| 5,176,137 A | 1/1993 | Erickson et al. |
| 5,178,350 A | 1/1993 | Vink et al. |
| 5,188,105 A | 2/1993 | Keimel |
| 5,191,884 A | 3/1993 | Gilli et al. |
| 5,193,535 A | 3/1993 | Bardy et al. |
| 5,257,621 A | 11/1993 | Bardy et al. |
| 5,312,443 A | 5/1994 | Adams et al. |
| 5,330,508 A | 7/1994 | Gunderson |
| 5,334,966 A | 8/1994 | Takeshima et al. |
| 5,447,519 A | 9/1995 | Peterson |
| 5,464,434 A | 11/1995 | Alt |
| 5,545,186 A | 8/1996 | Olson et al. |
| 5,593,431 A | 1/1997 | Sheldon |
| 5,687,733 A | 11/1997 | McKown |
| 5,720,295 A | 2/1998 | Greenhut et al. |
| 5,755,736 A | 5/1998 | Gillberg et al. |
| 5,755,737 A | 5/1998 | Prieve et al. |
| 5,755,739 A | 5/1998 | Sun et al. |
| 5,797,399 A | 8/1998 | Morris et al. |
| 5,800,465 A | 9/1998 | Thompson et al. |
| 5,836,975 A | 11/1998 | DeGroot |
| 5,846,263 A | 12/1998 | Peterson et al. |
| 5,855,593 A | 1/1999 | Olson et al. |
| 5,857,977 A | 1/1999 | Caswell et al. |
| 5,893,882 A | 4/1999 | Peterson et al. |
| 5,894,786 A | 4/1999 | Miya |
| 5,931,857 A | 8/1999 | Prieve et al. |
| 5,987,356 A | 11/1999 | DeGroot |
| 5,991,656 A | 11/1999 | Olson et al. |
| 6,052,620 A | 4/2000 | Gillberg et al. |
| 6,134,479 A | 10/2000 | Brewer et al. |
| 6,141,581 A | 10/2000 | Olson et al. |
| 6,178,350 B1 | 1/2001 | Olson et al. |
| 6,230,059 B1 | 5/2001 | Duffin |
| 6,236,882 B1 | 5/2001 | Lee et al. |
| 6,259,947 B1 | 7/2001 | Olson et al. |
| 6,287,328 B1 | 9/2001 | Snyder et al. |
| 6,304,773 B1 | 10/2001 | Taylor et al. |
| 6,364,251 B1 | 4/2002 | Yim |
| 6,397,100 B2 | 5/2002 | Stadler et al. |
| 6,449,503 B1 | 9/2002 | Hsu |
| 6,480,734 B1 | 11/2002 | Zhang et al. |
| 6,487,443 B2 | 11/2002 | Olson et al. |
| 6,618,622 B1 | 9/2003 | Mann et al. |
| 6,718,204 B2 | 4/2004 | DeGroot et al. |
| 6,731,978 B2 | 5/2004 | Olson et al. |
| 6,754,527 B2 | 6/2004 | Stroebel et al. |
| 6,754,528 B2 | 6/2004 | Bardy et al. |
| 6,862,477 B1 | 3/2005 | Mo |
| 6,879,856 B2 | 4/2005 | Stadler et al. |
| 6,892,094 B2 | 5/2005 | Ousdigian et al. |
| 6,925,329 B1 | 8/2005 | Sloman |
| 7,010,347 B2 | 3/2006 | Schecter |
| 7,027,858 B2 | 4/2006 | Cao et al. |
| 7,043,299 B2 | 5/2006 | Erlinger et al. |
| 7,065,410 B2 | 6/2006 | Bardy et al. |
| 7,076,289 B2 | 7/2006 | Sarkar et al. |
| 7,103,405 B2 | 9/2006 | Sarkar et al. |
| 7,103,464 B2 | 9/2006 | Zielke |
| 7,130,677 B2 | 10/2006 | Brown et al. |
| 7,149,577 B2 | 12/2006 | Sharma et al. |
| 7,151,962 B2 | 12/2006 | Belk |
| 7,184,831 B2 | 2/2007 | Belk |
| 7,194,302 B2 | 3/2007 | Bardy et al. |
| 7,239,925 B2 | 7/2007 | Bardy et al. |
| 7,248,921 B2 | 7/2007 | Palreddy et al. |
| 7,251,757 B2 | 7/2007 | Ouellette et al. |
| 7,274,962 B2 | 9/2007 | Bardy et al. |
| 7,299,092 B2 | 11/2007 | Bardy et al. |
| 7,299,097 B2 | 11/2007 | Bardy et al. |
| 7,317,942 B2 | 1/2008 | Brown |
| 7,330,757 B2 | 2/2008 | Ostroff et al. |
| 7,374,382 B2 | 5/2008 | Bentrim |
| 7,376,458 B2 | 5/2008 | Palreddy et al. |
| 7,379,772 B2 | 5/2008 | Bardy et al. |
| 7,392,082 B2 | 6/2008 | Sharma |
| 7,392,085 B2 | 6/2008 | Warren et al. |
| 7,406,350 B2 | 7/2008 | Erlinger et al. |
| 7,444,182 B2 | 10/2008 | Ostroff et al. |
| 7,477,935 B2 | 1/2009 | Palreddy et al. |
| 7,583,579 B2 | 9/2009 | Ueki |
| 7,623,909 B2 | 11/2009 | Sanghera et al. |
| 7,623,913 B2 | 11/2009 | Phillips |
| 7,627,367 B2 | 12/2009 | Warren et al. |
| 7,657,322 B2 | 2/2010 | Bardy et al. |
| 7,728,579 B2 | 6/2010 | Mueller |
| 7,734,333 B2 | 6/2010 | Ghanem et al. |
| 7,734,336 B2 | 6/2010 | Ghanem et al. |
| 7,742,812 B2 | 6/2010 | Ghanem et al. |
| 7,761,142 B2 | 7/2010 | Ghanem et al. |
| 7,761,150 B2 | 7/2010 | Ghanem et al. |
| 7,761,152 B2 | 7/2010 | Chen et al. |
| 7,769,452 B2 | 8/2010 | Ghanem et al. |
| 7,774,049 B2 | 8/2010 | Ghanem et al. |
| 7,774,616 B2 | 8/2010 | Dale et al. |
| 7,783,340 B2 | 8/2010 | Sanghera et al. |
| 7,822,471 B2 | 10/2010 | Bowers |
| 7,894,894 B2 | 2/2011 | Stadler et al. |
| 7,904,153 B2 | 3/2011 | Greenhut et al. |
| 7,907,993 B2 | 3/2011 | Ghanem et al. |
| 7,930,024 B2 | 4/2011 | Ousdigian |
| 7,937,135 B2 | 5/2011 | Ghanem et al. |
| 7,941,214 B2 | 5/2011 | Kleckner et al. |
| 7,991,459 B2 | 8/2011 | Palreddy et al. |
| 7,991,471 B2 | 8/2011 | Ghanem et al. |
| 7,996,082 B2 | 8/2011 | Palreddy et al. |
| 8,014,851 B2 | 9/2011 | Ostroff et al. |
| 8,027,720 B2 | 9/2011 | Bardy et al. |
| 8,027,791 B2 | 9/2011 | Soykan |
| 8,050,754 B2 | 11/2011 | Ostroff et al. |
| 8,068,901 B2 | 11/2011 | Ghanem et al. |
| 8,073,532 B2 | 12/2011 | Palreddy et al. |
| 8,095,206 B2 | 1/2012 | Ghanem et al. |
| 8,116,867 B2 | 2/2012 | Ostroff |
| 8,160,684 B2 | 4/2012 | Ghanem et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,170,663 B2 | 5/2012 | DeGroot et al. |
| 8,185,198 B2 | 5/2012 | Palreddy et al. |
| 8,200,341 B2 | 6/2012 | Sanghera et al. |
| 8,229,563 B2 | 7/2012 | Warren et al. |
| 8,249,702 B2 | 8/2012 | Warren et al. |
| 8,265,737 B2 | 9/2012 | Warren et al. |
| 8,265,749 B2 | 9/2012 | Allavatam et al. |
| 8,285,375 B2 | 10/2012 | Bardy et al. |
| 8,306,618 B2 | 11/2012 | Ghanem et al. |
| 8,332,022 B2 | 12/2012 | Brown et al. |
| 8,346,357 B2 | 1/2013 | Palreddy et al. |
| 8,364,251 B2 | 1/2013 | Phillips |
| 8,401,629 B2 | 3/2013 | Stadler et al. |
| 8,435,185 B2 | 5/2013 | Ghanem et al. |
| 8,437,838 B2 | 5/2013 | Warren et al. |
| 8,457,737 B2 | 6/2013 | Bardy et al. |
| 8,478,389 B1 | 7/2013 | Brockway et al. |
| 8,483,813 B2 | 7/2013 | Zhang et al. |
| 8,483,843 B2 | 7/2013 | Sanghera et al. |
| 8,494,630 B2 | 7/2013 | Palreddy et al. |
| 8,527,044 B2 | 9/2013 | Edwards et al. |
| 8,548,573 B2 | 10/2013 | Keefe |
| 8,565,878 B2 | 10/2013 | Allavatam et al. |
| 8,588,895 B2 | 11/2013 | Sanghera et al. |
| 8,588,896 B2 | 11/2013 | Allavatam et al. |
| 8,594,775 B2 | 11/2013 | Ghosh et al. |

(56) References Cited

U.S. PATENT DOCUMENTS

| | | |
|---|---|---|
| 8,594,786 B2 | 11/2013 | Ousdigian |
| 8,600,489 B2 | 12/2013 | Warren et al. |
| 8,611,996 B2 | 12/2013 | Donofrio et al. |
| 8,626,280 B2 | 1/2014 | Allavatam et al. |
| 8,626,285 B2 | 1/2014 | Palreddy et al. |
| 8,700,152 B2 | 4/2014 | Palreddy et al. |
| 8,712,523 B2 | 4/2014 | Sanghera et al. |
| 8,744,555 B2 | 6/2014 | Allavatam et al. |
| 8,750,989 B2 | 6/2014 | Bardy et al. |
| 8,781,567 B2 | 7/2014 | Phillips |
| 8,781,602 B2 | 7/2014 | Sanghera et al. |
| 8,788,023 B2 | 7/2014 | Sanghera et al. |
| 8,825,157 B2 | 9/2014 | Warren et al. |
| 8,983,586 B2 | 3/2015 | Zhang |
| 9,278,226 B2 * | 3/2016 | Olson .................. A61N 1/3906 |
| 9,610,025 B2 | 4/2017 | Zhang |
| 10,376,705 B2 | 8/2019 | Zhang et al. |
| 11,602,639 B2 | 3/2023 | Zhang et al. |
| 2002/0058878 A1 | 5/2002 | Kohler et al. |
| 2002/0165459 A1 | 11/2002 | Starobin et al. |
| 2003/0083587 A1 | 5/2003 | Ferek-Petric |
| 2003/0097153 A1 | 5/2003 | Bardy et al. |
| 2003/0120312 A1 | 6/2003 | Cammilli et al. |
| 2004/0021523 A1 | 2/2004 | Sadowy et al. |
| 2004/0030256 A1 | 2/2004 | Lin |
| 2004/0049120 A1 | 3/2004 | Cao et al. |
| 2004/0059237 A1 | 3/2004 | Narayan et al. |
| 2004/0088018 A1 | 5/2004 | Sawchuk et al. |
| 2004/0093037 A1 | 5/2004 | Henry |
| 2004/0111121 A1 | 6/2004 | Brown et al. |
| 2004/0220635 A1 | 11/2004 | Burnes |
| 2004/0254613 A1 | 12/2004 | Ostroff et al. |
| 2005/0038478 A1 | 2/2005 | Klepfer et al. |
| 2006/0025822 A1 | 2/2006 | Zhang |
| 2006/0042809 A1 | 3/2006 | Neufeld et al. |
| 2006/0074331 A1 | 4/2006 | Kim et al. |
| 2006/0217621 A1 | 9/2006 | Kim et al. |
| 2007/0123940 A1 | 5/2007 | Dorr et al. |
| 2007/0232948 A1 | 10/2007 | Stadler et al. |
| 2007/0233196 A1 | 10/2007 | Stadler et al. |
| 2007/0233198 A1 | 10/2007 | Ghanem et al. |
| 2007/0239220 A1 | 10/2007 | Greenhut et al. |
| 2007/0270704 A1 | 11/2007 | Ghanem et al. |
| 2007/0276445 A1 | 11/2007 | Sanghera et al. |
| 2007/0276452 A1 | 11/2007 | Sanghera et al. |
| 2008/0103535 A1 | 5/2008 | Ostroff et al. |
| 2008/0132965 A1 | 6/2008 | Ostroff et al. |
| 2008/0269813 A1 | 10/2008 | Greenhut et al. |
| 2008/0275516 A1 * | 11/2008 | Ghanem .................. A61B 5/352 607/9 |
| 2008/0275521 A1 | 11/2008 | Warren et al. |
| 2008/0288009 A1 | 11/2008 | Kim et al. |
| 2009/0005828 A1 | 1/2009 | Levine |
| 2009/0054938 A1 | 2/2009 | Ostroff et al. |
| 2010/0004713 A1 | 1/2010 | Warren et al. |
| 2010/0023083 A1 | 1/2010 | Eisinger et al. |
| 2010/0114196 A1 | 5/2010 | Burnes et al. |
| 2010/0331904 A1 | 12/2010 | Warren et al. |
| 2011/0270102 A1 | 11/2011 | Zhang et al. |
| 2011/0270103 A1 | 11/2011 | Zhang et al. |
| 2011/0270107 A1 | 11/2011 | Zhang et al. |
| 2011/0270110 A1 | 11/2011 | Zhang et al. |
| 2011/0307024 A1 | 12/2011 | Ostroff et al. |
| 2011/0319953 A1 | 12/2011 | Reed et al. |
| 2012/0029335 A1 | 2/2012 | Sudam et al. |
| 2012/0095520 A1 | 4/2012 | Zhang et al. |
| 2012/0316612 A1 | 12/2012 | Warren et al. |
| 2013/0030481 A1 | 1/2013 | Ghosh et al. |
| 2013/0109985 A1 | 5/2013 | Gillberg et al. |
| 2013/0197381 A1 | 8/2013 | Charlton et al. |
| 2013/0261471 A1 | 10/2013 | Saha et al. |
| 2014/0275917 A1 | 9/2014 | Allavatam et al. |
| 2014/0296932 A1 | 10/2014 | Sanghera et al. |
| 2015/0046396 A1 | 2/2015 | Limaye et al. |
| 2015/0133954 A1 | 5/2015 | Seifert et al. |

FOREIGN PATENT DOCUMENTS

| | | |
|---|---|---|
| CN | 101232844 A | 7/2008 |
| CN | 103110417 A | 5/2013 |
| EP | 1631352 B1 | 11/2008 |
| EP | 1659934 B1 | 11/2008 |
| EP | 2029224 A1 | 3/2009 |
| EP | 1615693 B1 | 1/2011 |
| EP | 1827598 B1 | 3/2012 |
| EP | 2313153 B1 | 4/2012 |
| EP | 2029226 B1 | 7/2012 |
| EP | 1631350 B1 | 8/2012 |
| EP | 2025363 B1 | 1/2013 |
| EP | 1774906 B1 | 5/2013 |
| EP | 2268358 B1 | 5/2013 |
| EP | 2446925 B1 | 6/2013 |
| EP | 2446926 B1 | 6/2013 |
| EP | 2455132 B1 | 6/2013 |
| EP | 2077889 B1 | 7/2013 |
| EP | 1803485 B1 | 1/2014 |
| EP | 1803486 B1 | 2/2014 |
| EP | 2166938 B1 | 8/2014 |
| EP | 2029225 B1 | 8/2016 |
| EP | 2268357 B1 | 11/2016 |
| EP | 2459275 B1 | 1/2018 |
| EP | 2114244 B1 | 8/2018 |
| EP | 1827220 B1 | 11/2018 |
| WO | 199805254 A1 | 2/1998 |
| WO | 200047278 A1 | 8/2000 |
| WO | 2004093974 A2 | 11/2004 |
| WO | 2004105871 A1 | 12/2004 |
| WO | 201136916 A1 | 3/2011 |
| WO | 2012075119 A1 | 6/2012 |

OTHER PUBLICATIONS

C00007516.WOU2 (PCT/US2015/026277) PCT Notification of Transmittal of the International Search Report and the Written Opinion of the International Searching Authority, Mailed Jun. 26, 2015, 11 pp.

C00007576.WOU7 (PCT/US2015/026743) PCT Notification of Transmittal of the International Search Report and the Written Opinion of the International Searching Authority, mailed Jul. 29, 2015, 10 pp.

C00007576.WOU8 (PCT/US20 15/0267 45) PCT Notification of Transmittal of the International Search Report and the Written Opinion of the International Searching Authority, mailed Aug. 6, 2015, 8 pp.

C00007576.WOU9 (PCT/US20 15/026,954) PCT Notification of Transmittal of the International Search Report and the Written Opinion of the International Searching Authority, mailed Jul. 29, 2015, 11 pp.

C00008145.WOU3 (PCT/US2015/032809) PCT Notification of Transmittal of the International Search Report and the Written Opinion of the International Searching Authority, mailed Aug. 6, 2015, 11 pp.

Corrected Notice of Allowance from U.S. Appl. No. 16/537,969 dated Feb. 15, 2023, 2 pp.

Decision on Rejection and translation thereof from counterpart Chinese Application No. 201911285556.9 dated May 10, 2022, 10 pp.

European Communication dated Mar. 27, 2020, corresponding to counterpart European Application No. 15718710.5 (C00007180. EPN4); 5 pp.

European Communication dated May 19, 2020, corresponding to counterpart European Application No. 15715119.2; (P0040072. EPN8); 4 pp.

First Office Action and Search Report, and translation thereof, from counterpart Chinese Application No. 202010477495.2 dated Nov. 10, 2022, 5 pp.

Notice of Allowance from U.S. Appl. No. 16/537,969 dated Nov. 7, 2022, 8 pp.

(PCT/US2015/023335) PCT Notification of Transmittal of the International Search Report and the Written Opinion of the International Searching Authority, Mailed Jun. 18, 2015, 11 pp.

(PCT/US2015/023341) PCT Notification of Transmittal of the International Search Report and the Written Opinion of the International Searching Authority, Mailed Jun. 18, 2015, 10 pp.

(56) References Cited

OTHER PUBLICATIONS (PCT/US2015/023351) PCT Notification of Transmittal of the International Search Report and the Written Opinion of the International Searching Authority, Mailed Jun. 3, 2015, 12 pp.

Prosecution History from U.S. Appl. No. 16/537,969, now issued U.S. Pat. No. 11,602,639, dated Jun. 12, 2020 through Feb. 15, 2023, 70 pp.

Prosecution History from U.S. Appl. No. 14/242,391, now issued U.S. Pat. No. 10,376,705 dated Jan. 21, 2016 through Jul. 12, 2019, 125 pp.

Zhang et al., "Method and Apparatus for Discriminating Tachycardia Events in a Medical Device," Notice on First Office Action, Chinese Application No. 201580017981.3, Dispatched on Aug. 3, 2018, 11 pp.

Zhang et al., "Method and Apparatus for Discriminating Tachycardia Events in a Medical Pevice," Notice on First Office Action, Chinese Application No. 201580017982.8, Dispatched on Aug. 3, 2018, 10 pp.

* cited by examiner

METHOD AND APPARATUS FOR DISCRIMINATING TACHYCARDIA EVENTS IN A MEDICAL DEVICE

RELATED APPLICATION

This application is a Divisional of U.S. patent application Ser. No. 16/537,969, entitled "METHOD AND APPARATUS FOR DISCRIMINATING TACHYCARDIA EVENTS IN A MEDICAL DEVICE," filed Aug. 12, 2019, which is a Continuation of U.S. patent application Ser. No. 14/242,391, (now U.S. Pat. No. 10,376,705 issued Aug. 13, 2019), entitled "METHOD AND APPARATUS FOR DISCRIMINATING TACHYCARDIA EVENTS IN A MEDICAL DEVICE," filed Apr. 1, 2014, both of which are incorporated herein by reference in their entirety.

TECHNICAL FIELD

The disclosure relates generally to implantable medical devices and, in particular, to an apparatus and method for discriminating arrhythmias and delivering a therapy in a medical device.

BACKGROUND

Implantable medical devices are available for treating cardiac tachyarrhythmias by delivering anti-tachycardia pacing therapies and electrical shock therapies for cardioverting or defibrillating the heart. Such a device, commonly known as an implantable cardioverter defibrillator or "ICD", senses electrical activity from the heart, determines a patient's heart rate, and classifies the rate according to a number of heart rate zones in order to detect episodes of ventricular tachycardia or fibrillation. Typically a number of rate zones are defined according to programmable detection interval ranges for detecting slow ventricular tachycardia, fast ventricular tachycardia and ventricular fibrillation. Intervals between sensed R-waves, corresponding to the depolarization of the ventricles, are measured. Sensed R-R intervals falling into defined detection interval ranges are counted to provide a count of ventricular tachycardia (VT) or ventricular fibrillation (VF) intervals, for example. A programmable number of intervals to so detect (NID) defines the number of tachycardia intervals occurring consecutively or out of a given number of preceding event intervals that are required to detect VT or VF.

Tachyarrhythmia detection may begin with detecting a fast ventricular rate, referred to as rate- or interval-based detection. Once VT or VF is detected based on rate, the morphology of the sensed depolarization signals, e.g. wave shape, amplitude or other features, may be used in discriminating heart rhythms to improve the sensitivity and specificity of tachyarrhythmia detection methods.

A primary goal of a tachycardia detection algorithm is to rapidly respond to a potentially malignant rhythm with a therapy that will terminate the arrhythmia with high certainty. Another goal, however, is to avoid excessive use of ICD battery charge, which shortens the life of the ICD, e.g. due to delivering unnecessary therapies or therapies at a higher voltage than needed to terminate a detected tachyarrhythmia. Minimizing the patient's exposure to painful shock therapies is also an important consideration. Accordingly, a need remains for ICDs that perform tachycardia discrimination with high specificity and control therapy delivery to successfully terminate a detected VT requiring therapy while conserving battery charge and limiting patient exposure to delivered shock therapy by withholding therapy delivery whenever possible in situations where the therapy may not be required.

DETAILED DESCRIPTION

Figure 1:
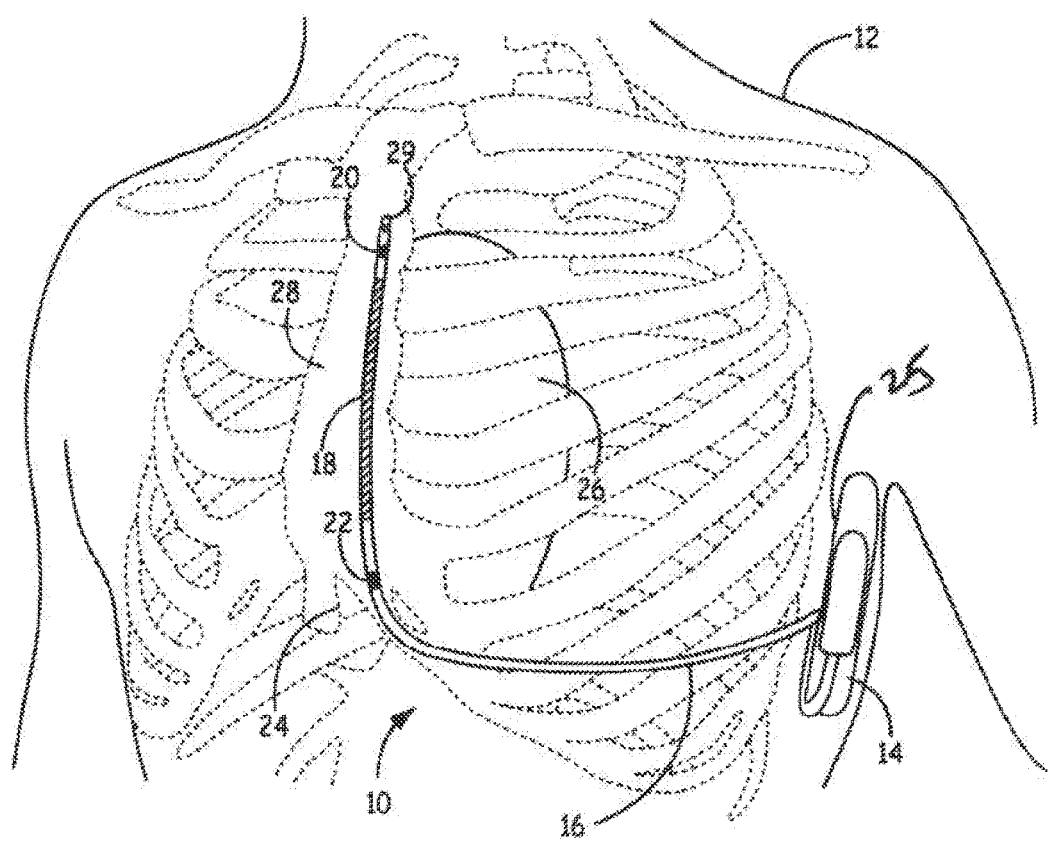
FIG. 1 is a conceptual diagram of a patient implanted with an example extravascular cardiac defibrillation system.

FIG. 1 is a conceptual diagram of a patient 12 implanted with an example extravascular cardiac defibrillation system 10. In the example illustrated in FIG. 1, extravascular cardiac defibrillation system 10 is an implanted subcutaneous ICD system. However, the techniques of this disclosure may also be utilized with other extravascular implanted cardiac defibrillation systems, such as a cardiac defibrillation system having a lead implanted at least partially in a substernal or submuscular location. Additionally, the techniques of this disclosure may also be utilized with other implantable systems, such as implantable pacing systems, implantable neurostimulation systems, drug delivery systems or other systems in which leads, catheters or other components are implanted at extravascular locations within patient 12. This disclosure, however, is described in the context of an implantable extravascular cardiac defibrillation system for purposes of illustration.

Extravascular cardiac defibrillation system 10 includes an implantable cardioverter defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24, defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

Defibrillation lead 16 is placed along sternum 28 such that a therapy vector between defibrillation electrode 18 and a second electrode (such as a housing or can 25 of ICD 14 or an electrode placed on a second lead) is substantially across the ventricle of heart 26. The therapy vector may, in one example, be viewed as a line that extends from a point on the defibrillation electrode 18 to a point on the housing or can 25 of ICD 14. In another example, defibrillation lead 16 may be placed along sternum 28 such that a therapy vector between defibrillation electrode 18 and the housing or can 25 of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or more centrally located over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example: the distal end of defibrillation lead 16 may be positioned near the second or third rib of patient 12. However, the distal end of defibrillation lead 16 may be positioned further superior or inferior depending on the location of ICD 14, location of electrodes 18, 20, and 22, or other factors.

Although ICD 14 is illustrated as being implanted near a midaxillary line of patient 12. ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing or can 25 that forms a hermetic seal that protects components within ICD 14. The housing 25 of ICD 14 may be formed of a conductive material, such as titanium or other biocompatible conductive material or a combination of conductive and non-conductive materials. In some instances, the housing 25 of ICD 14 functions as an electrode (referred to as a housing electrode or can electrode) that is used in combination with one of electrodes 18, 20, or 22 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. Housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 18, 20, and 22. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 18, 20 and 22, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 18, 20 and 22. In other words, each of the one or more elongated electrical conductors contained within the lead body of defibrillation lead 16 may engage with respective ones of electrodes 18, and 22. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 18, 20 and 22 and transmit sensed electrical signals from one or more of electrodes 18, 20 and 22 to the sensing module within ICD 14.

ICD 14 may sense electrical activity of heart 26 via one or more sensing vectors that include combinations of electrodes 20 and 22 and the housing or can of ICD 14. For example, ICD 14 may obtain electrical signals sensed using a sensing vector between electrodes 20 and 22, obtain electrical signals sensed using a sensing vector between electrode 20 and the conductive housing or can of ICD 14, obtain electrical signals sensed using a sensing vector between electrode 22 and the conductive housing or can 25 of ICD 14, or a combination thereof. In some instances, ICD 14 may sense cardiac electrical signals using a sensing vector that includes defibrillation electrode 18, such as a sensing vector between defibrillation electrode 18 and one of electrodes 20 or 22, or a sensing vector between defibrillation electrode 18 and the housing or can 25 of ICD 14.

ICD may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 18 of defibrillation lead 16 and the housing or can 25. Defibrillation electrode 18 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 20 and 22 and/or the housing or can 25. Electrodes 20 and 22 may comprise ring electrodes, hemispherical electrodes, coil electrodes, helix electrodes, segmented electrodes, directional electrodes, or other types of electrodes, or combination thereof. Electrodes 20 and 22 may be the same type of electrodes or different types of electrodes, although in the example of FIG. 1 both electrodes 20 and 22 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 22 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum 28. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the subxiphoid or inferior xiphoid area, near the apex of the heart, or other location not in direct contact with heart 26 and not subcutaneous. In still further instances, the lead may be implanted at a pericardial or epicardial location outside of the heart 26.

Figure 2:
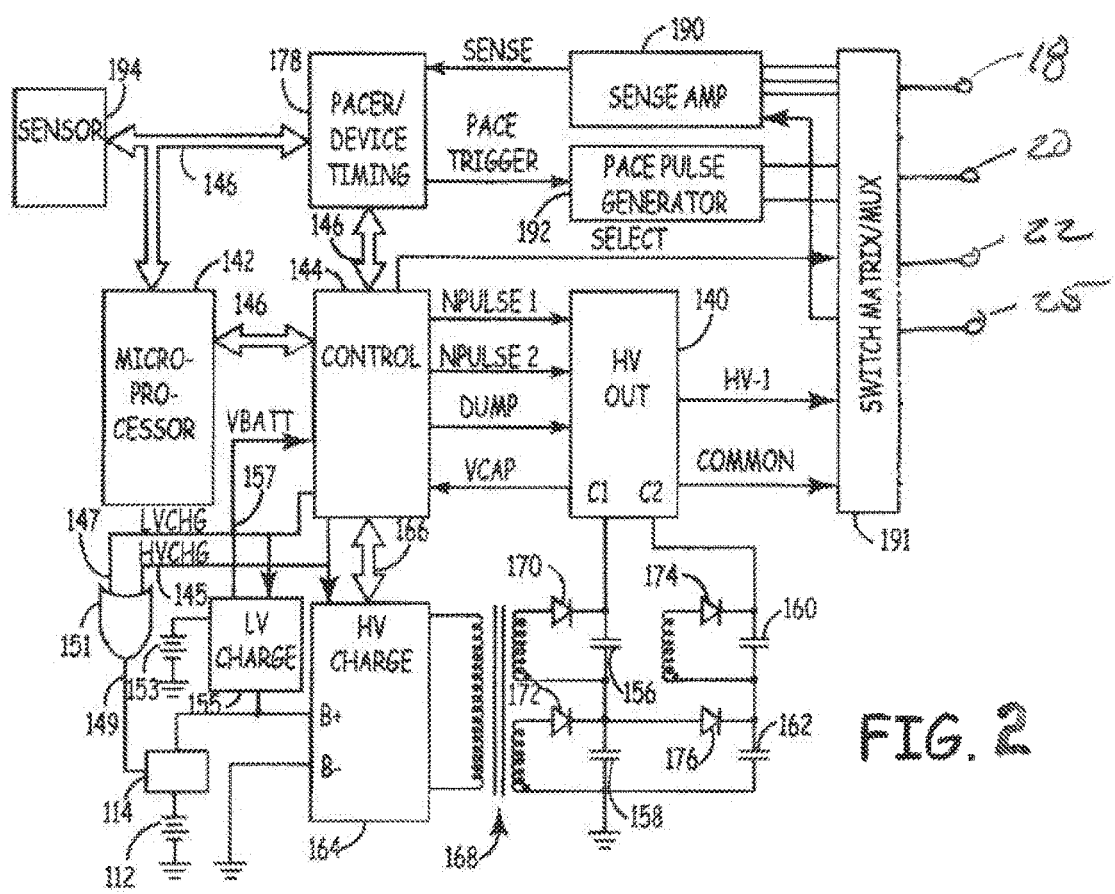
FIG. 2 is an exemplary schematic diagram of electronic circuitry within a hermetically sealed housing of a subcutaneous device according to an embodiment of the present invention.

FIG. 2 is an exemplary schematic diagram of electronic circuitry within a hermetically sealed housing of a subcutaneous device according to an embodiment of the present invention. As illustrated in FIG. 2, subcutaneous device 14 includes a low voltage battery 153 coupled to a power supply (not shown) that supplies power to the circuitry of the subcutaneous device 14 and the pacing output capacitors to supply pacing energy in a manner well known in the art. The low voltage battery 153 may be formed of one or two conventional $LiCF_x$, $LiMnO_2$ or $LiI_2$ cells, for example. The subcutaneous device 14 also includes a high voltage battery 112 that may be formed of one or two conventional LiSVO or $LiMnO_2$ cells. Although two both low voltage battery and a high voltage battery are shown in FIG. 2, according to an embodiment of the present invention, the device 14 could utilize a single battery for both high and low voltage uses.

Further referring to FIG. 2, subcutaneous device 14 functions are controlled by means of software, firmware and hardware that cooperatively monitor the ECG signal, determine when a cardioversion-defibrillation shock or pacing is necessary, and deliver prescribed cardioversion-defibrillation and pacing therapies. The subcutaneous device 14 may incorporate circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks typically employing ICD IPG housing electrodes 28 coupled to the COMMON output 123 of high voltage output circuit 140 and cardioversion-defibrillation electrode 24 disposed posteriorly and subcutaneously and coupled to the HVI output 113 of the high voltage output circuit 140.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The subcutaneous device 14 of the present invention uses maximum voltages in the range of about 300 to approximately 1000 Volts and is associated with energies of approximately 25 to 150 joules or more. The total high voltage capacitance could range from about 50 to about 300 microfarads. Such cardioversion-defibrillation shocks are only delivered when a malignant tachyarrhythmia, e.g., ventricular fibrillation is detected through processing of the far field cardiac ECG employing the detection algorithms as described herein below.

In FIG. 2, sense amp 190 in conjunction with pacer/device timing circuit 178 processes the far field ECG sense signal that is developed across a particular ECG sense vector defined by a selected pair of the subcutaneous electrodes 18, 20, 22 and the can or housing 25 of the device 14, or, optionally, a virtual signal (i.e., a mathematical combination of two vectors) if selected. The selection of the sensing electrode pair is made through the switch matrix/MUX 191 in a manner to provide the most reliable sensing of the ECG signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the Control circuit 144 as a function of the intervals between R-wave sense event signals that are output from the pacer/device timing 178 and sense amplifier circuit 190 to the timing and control circuit 144. It should be noted that the present invention utilizes not only interval based signal analysis method but also supplemental sensors and morphology processing method and apparatus as described herein below.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the subcutaneous device pocket or, alternatively, located on the lead 18 to enable the sensing of contacting or near-contacting tissue oxygenation or color.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 300-1000V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 may be charged, for example, by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 18 and 25 coupled to the HV-1 and COMMON output as shown in FIG. 2.

Thus, subcutaneous device 14 monitors the patient's status and initiates the delivery of a cardioversion-defibrillation shock through the cardioversion-defibrillation electrodes 18 and 25 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. The subcutaneous device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated ICD.

Subcutaneous device 14 desirably includes telemetry circuit (not shown in FIG. 2), so that it is capable of being programmed by means of external programmer 20 via a 2-way telemetry link (not shown). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minnesota.

Various telemetry systems for providing the necessary communications channels between an external programming unit and an implanted device have been developed and are well known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

According to an embodiment of the present invention, in order to automatically select the preferred ECG vector set, it is necessary to have an index of merit upon which to rate the quality of the signal. "Quality" is defined as the signal's ability to provide accurate heart rate estimation and accurate morphological waveform separation between the patient's usual sinus rhythm and the patient's ventricular tachyarrhythmia.

Appropriate indices may include R-wave amplitude, R-wave peak amplitude to waveform amplitude between R-waves (i.e., signal to noise ratio), low so slope content, relative high versus low frequency power, mean frequency estimation, probability density function, or some combination of these metrics.

Automatic vector selection might be done at implantation or periodically (daily, weekly, monthly) or both. At implant, automatic vector selection may be initiated as part of an automatic device turn-on procedure that performs such activities as measure lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG vector quality is adequate for the current patient and for the device and lead position, prior to suturing the subcutaneous device 14 device in place and closing the incision. Such an ECG quality indicator would allow the implanting physician to maneuver the device to a new location or orientation to improve the quality of the ECG signals as required. The preferred ECG vector or vectors may also be selected at implant as part of the device turn-on procedure. The preferred vectors might be those vectors with the indices that maximize rate estimation and detection accuracy. There may also be an a priori set of vectors that are preferred by the physician, and as long as those vectors exceed some minimum threshold, or are only slightly worse than some other more desirable vectors, the a priori preferred vectors are chosen. Certain vectors may be considered nearly identical such that they are not tested unless the a priori selected vector index falls below some predetermined threshold.

Depending upon metric power consumption and power requirements of the device, the ECG signal quality metric may be measured on the range of vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the subcutaneous device 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep (using an internal clock (e.g., 2:00 am) or, alternatively, infer sleep by determining the patient's position (via a 2- or 3-axis accelerometer) and a lack of activity).

If infrequent automatic, periodic measurements are made, it may also be desirable to measure noise (e.g., muscle, motion. EMI, etc.) in the signal and postpone the vector selection measurement when the noise has subsided.

Subcutaneous device 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture.

In the preferred embodiment, vector quality metric calculations would occur a number of times over approximately 1 minute, once per day, for each vector. These values would be averaged for each vector over the course of one week. Averaging may consist of a moving average or recursive average depending on time weighting and memory considerations. In this example, the preferred vector(s) would be selected once per week.

Figure 3:
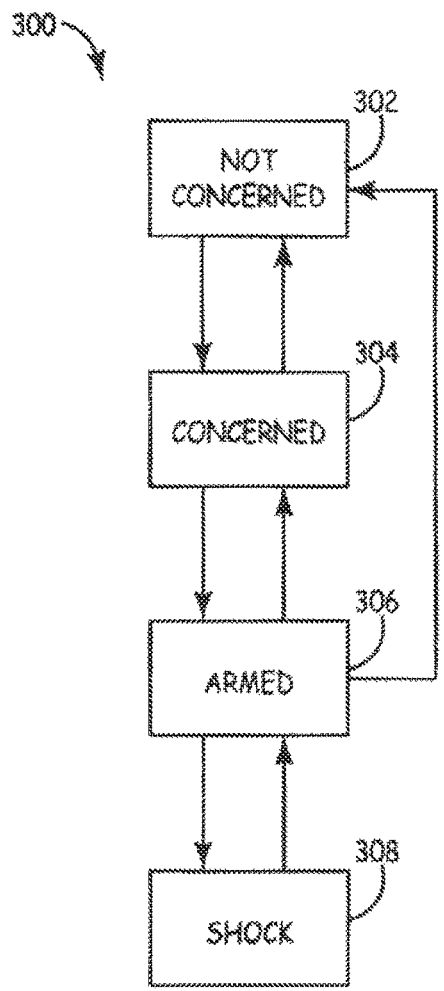
FIG. 3 is a state diagram of detection of arrhythmias in a medical device according to an embodiment of the present invention.

FIG. 3 is a state diagram of detection of arrhythmias in a medical device according to an embodiment of the present invention. As illustrated in FIG. 3, during normal operation, the device 14 is in a not concerned state 302, during which R-wave intervals are being evaluated to identify periods of rapid rates and/or the presence of asystole. Upon detection of short R-wave intervals simultaneously in two separate ECG sensing vectors, indicative of an event that, if confirmed, may require the delivery of therapy, the device 14 transitions from the not concerned state 302 to a concerned state 304. In the concerned state 304 the device 14 evaluates a predetermined window of ECG signals to determine the likelihood that the signal is corrupted with noise and to discriminate rhythms requiring shock therapy from those that do not require shock therapy, using a combination of R-wave intervals and ECG signal morphology information.

If a rhythm requiring shock therapy continues to be detected while in the concerned state 304, the device 14 transitions from the concerned state 304 to an armed state 306. If a rhythm requiring shock therapy is no longer detected while the device is in the concerned state 304 and the R-wave intervals are determined to no longer be short, the device 14 returns to the not concerned state 302. However, if a rhythm requiring shock therapy is no longer detected while the device is in the concerned state 304, but the R-wave intervals continue to be detected as being short, processing continues in the concerned state 304.

In the armed state 306, the device 14 charges the high voltage shocking capacitors and continues to monitor R-wave intervals and ECG signal morphology for spontaneous termination. If spontaneous termination of the rhythm requiring shock therapy occurs, the device 14 returns to the not concerned state 302. If the rhythm requiring shock therapy is still determined to be occurring once the charging of the capacitors is completed, the device 14 transitions from the armed state 306 to a shock state 308. In the shock state 308, the device 14 delivers a shock and returns to the armed state 306 to evaluate the success of the therapy delivered.

The transitioning between the not concerned state 302, the concerned state 304, the armed state 306 and the shock state 308 may be performed as described in detail in U.S. Pat. No. 7,894,894 to Stadler et al., incorporated herein by reference in it's entirety.

Figure 4:
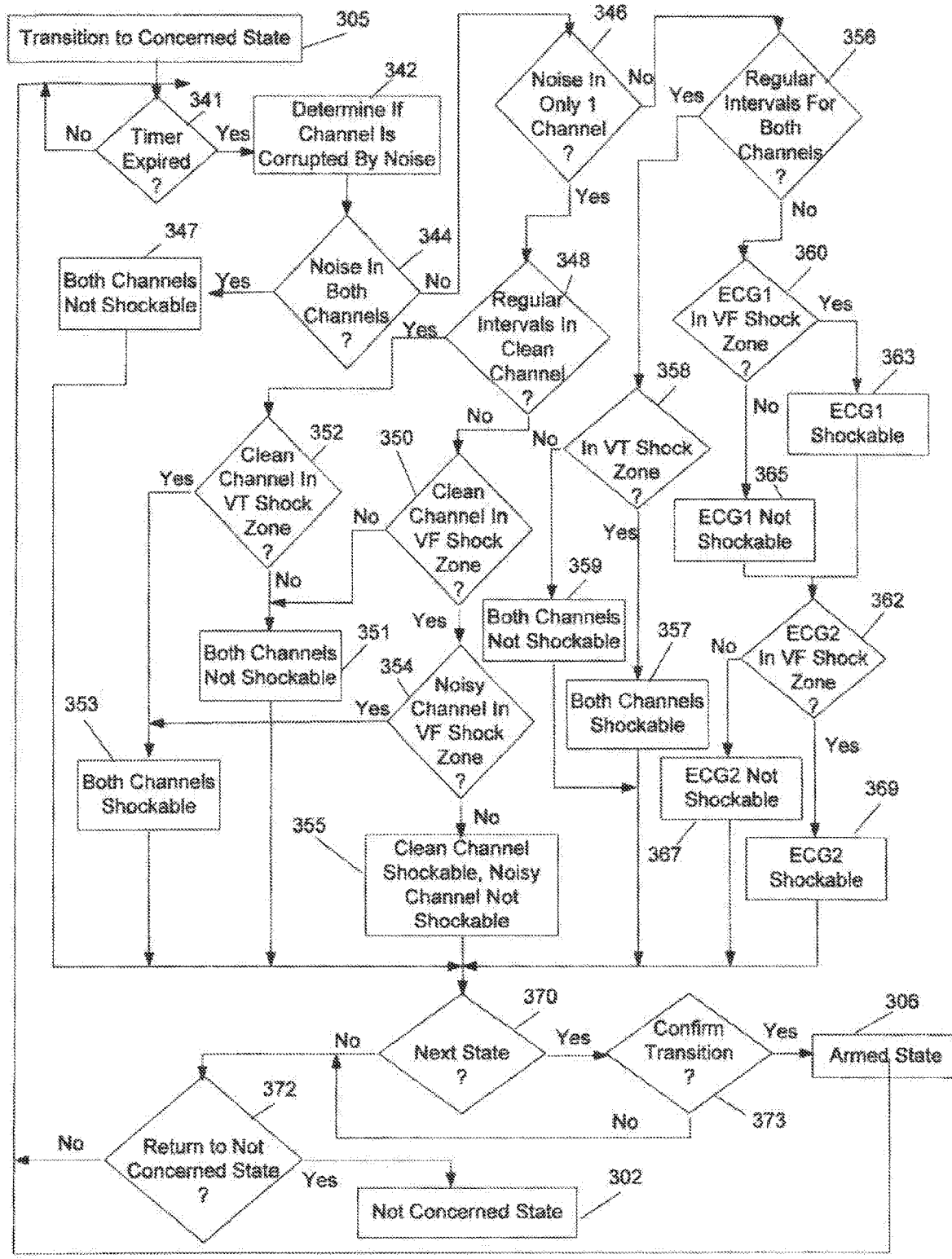
FIG. 4 is a flowchart of a method for detecting arrhythmias in a subcutaneous device according to an embodiment of the present disclosure.

FIG. 4 is a flowchart of a method for detecting arrhythmias in a subcutaneous device according to an embodiment of the present disclosure. As illustrated in FIG. 4, device 14 continuously evaluates the two channels ECG1 and ECG2 associated with two predetermined electrode vectors to determine when sensed events occur. For example, the electrode vectors for the two channels ECG1 and ECG2 may include a first vector (ECG1) selected between electrode positioned on lead 16 and the housing or can 25 of ICD 14, while the other electrode vector (ECG 2) is a vertical electrode vector between electrode 20 and electrode 22 positioned along the lead 16. However, the two sensing channels may in any combination of possible vectors, including those formed by the electrodes shown in FIG. 2, or other additional electrodes (not shown) that may be included along the lead or positioned along the housing of ICD 14.

According to an embodiment of the present application, for example, the device 14 determines whether to transition from the not concerned state 302 to the concerned state 304 by determining a heart rate estimate in response to the sensing of R-waves, as described in U.S. Pat. No. 7,894,894 to Stadler et al., incorporated herein by reference in it's entirety.

Upon transition from the not concerned state to the concerned state, Block 305, a most recent window of ECG data from both channels ECG1 and ECG2 are utilized, such as three seconds, for example, so that processing is triggered in the concerned state 304 by a three-second timeout, rather than by the sensing of an R-wave, which is utilized when in the not concerned state 302. It is understood that while the processing is described as being triggered over a three second period, other times periods for the processing time utilized when in the concerned state 304 may be chosen, but should preferably be within a range of 0.5 to 10 seconds. As a result, although sensing of individual R-waves continues to occur in both channels ECG1 and ECG2 when in the concerned state 304, and the buffer of 12 R-R intervals continues to be updated, the opportunities for changing from the concerned state 304 to another state and the estimates of heart rate only occur once the three-second timer expires. Upon initial entry to the concerned state 304, it is advantageous to process the most recent three-seconds of ECG data, i.e., ECG data for the three seconds leading up to the transition to the concerned state 304. This requires a continuous circular buffering of the most recent three seconds of ECG data even while in the not concerned state 302.

While in the concerned state 304, the present invention determines how sinusoidal and how noisy the signals are in order to determine the likelihood that a ventricular fibrillation (VF) or fast ventricular tachycardia (VT) event is taking place, since the more sinusoidal and low noise the signal is, the more likely a VT/VF event is taking place. As illustrated in FIG. 4, once the device transitions from the not concerned state 302 to the concerned state 304, Block 305, a buffer for each of the two channels ECG 1 and ECG2 for storing classifications of 3-second segments of data as "shockable" or "non-shockable" is cleared. Processing of signals of the two channels ECG1 and ECG2 while in the concerned state 304 is then triggered by the three second time period, rather than by the sensing of an R-wave utilized during the not concerned state 302.

Once the three second time interval has expired, YES in Block 341, morphology characteristics of the signal during the three second time interval for each channel are utilized to determine whether the signals are likely corrupted by noise artifacts and to characterize the morphology of the signal as "shockable" or "not shockable". For example, using the signals associated with the three second time interval, a determination is made for each channel ECG1 and ECG 2 as to whether the channel is likely corrupted by noise, Block 342, and a determination is then made as to whether both channels ECG1 and ECG2 are corrupted by noise, Block 344. The determination as to whether both channels are corrupted by noise may be made using known noise detection methods, such as the noise detection described in U.S. Pat. No. 7,894,894 to Stadler et al., incorporated herein by reference in it's entirety.

Once the determination as to whether the channels ECG1 and ECG2 are corrupted by noise is made, Block 342, a determination is made as to whether both channels are determined to be noise corrupted, Block 344. If the signal associated with both channels ECG1 and ECG2 is determined to likely be corrupted by noise, both channels are classified as being not shockable, Block 347, and therefore a buffer for each channel ECG1 and ECG 2 containing the last three classifications of the channel is updated accordingly. If both channels ECG1 and ECG2 are not determined to be likely corrupted by noise, No in Block 344, the device distinguishes between either one of the channels being not corrupted by noise or both channels being not corrupted by noise by determining whether noise was determined to be likely in only one of the two channels ECG1 and ECG2, Block 346.

If noise was likely in only one of the two channels, a determination is made whether the signal for the channel not corrupted by noise, i.e., the clean channel, is more likely associated with a VT event or with a VF event by determining, for example, whether the signal for that channel includes R-R intervals that are regular and the channel can be therefore classified as being relatively stable, Block 348. If the R-R intervals are determined not to be relatively stable, NO in Block 348, the signal for that channel is identified as likely being associated with VF, which is then verified by determining whether the signal is in a VF shock zone, Block 350, described below. If R-R intervals for that channel are determined to be stable, YES in Block 348, the signal is identified as likely being associated with VT, which is then verified by determining whether the signal is in a VT shock zone, Block 352, described below.

If noise was not likely for both of the channels, No in Block 346, i.e., both channels are determined to be clean channels, a determination is made whether the signal for both channels is more likely associated with a VT event or with a VF event by determining whether the signal for both channels includes R-R intervals that are regular and can be therefore classified as being relatively stable, Block 356, The determination in Block 356 of whether the R-R intervals are determined to be relatively stable may be made using the method described in U.S. Pat. No. 7,894,894 to Stadler et al., incorporated herein by reference in it's entirety. If the R-R intervals are determined not to be relatively stable, NO in Block 356, the signal for both channels is identified as likely being associated with VF, which is then verified by determining whether the signal for each channel is in a VF shock zone, Block 360, described below. If R-R intervals for both channels are determined to be stable, YES in Block 356, the signal is identified as likely being associated with VT, which is then verified by determining, based on both channels, whether the signal is in a VT shock zone. Block 358.

Figure 5:
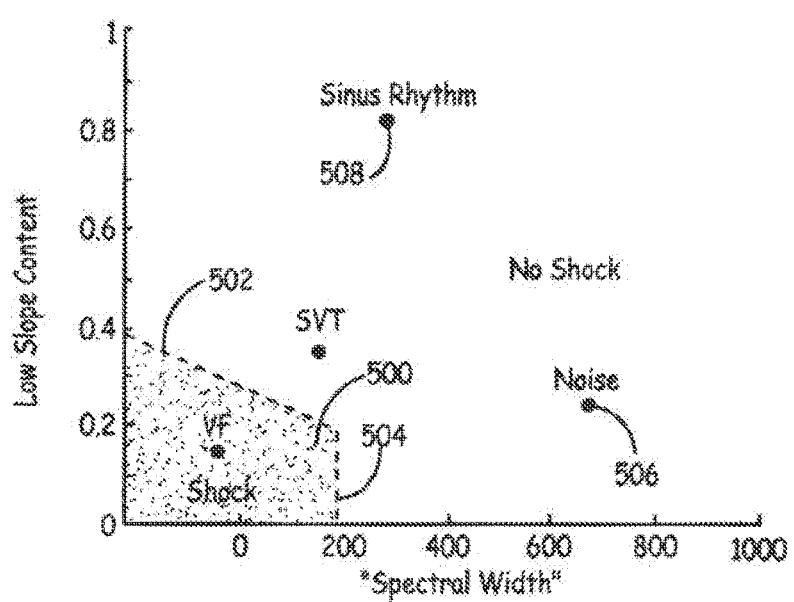
FIG. 5 is a graphical representation of a VF shock zone according to an embodiment of the present invention.

FIG. 5 is a graphical representation of a VF shock zone according to an embodiment of the present invention. As illustrated in FIG. 5, a VF shock zone 500 is defined for each channel ECG1 and ECG2 based on the relationship between the calculated low slope content and the spectral width associated with the channel. For example, the shock zone is defined by a first boundary 502 associated with the low slope content set for by the equation:

Low slope content=−0.0013×spectral width+0.415  Equation 1 and a second boundary 504 associated with the spectral width set forth by the equation:

spectral width=200  Equation 2

The low slope content metric is calculated as the ratio of the number of data points with low slope to the total number of samples in the 3-second segment. For example, according to an embodiment of the present invention, the difference between successive ECG samples is determined as an approximation of the first derivative (i.e, the slope) of the ECG signal. In particular, the raw signal for each channel is applied to a first order derivative filter to obtain a derivative signal for the three-second segment. The derivative signal is then rectified, divided into four equal sub-segments, and the largest absolute slope is estimated for each of the four sub-segments.

A determination is made as to whether the largest absolute slopes are less than a portion of the overall largest absolute slope for the whole three-second segment, such as one-fifth of the overall absolute slope, for example. If the largest absolute slope is less than the portion of the overall slope, then the slope value for that sub-segment is set equal to the overall largest absolute slope. If the largest absolute slope is not less than the portion of the overall slope, then the slope value for that sub-segment is set equal to the determined largest absolute slope for the sub-segment.

Once the slope value for each of the sub-segments has been determined and updated by being set equal to the largest slope for the three second segment, if necessary, the average of the four slopes is calculated and divided by a predetermined factor, such as 16 for example, to obtain a low slope threshold. The low slope content is then obtained by determining the number of sample points in the three-second segment having an absolute slope less than or equal to the low slope threshold.

According to an embodiment of the present invention, if, during the determination of the low slope threshold, the low slope threshold is a fraction, rather than a whole number, a correction is made to the low slope content to add a corresponding fraction of the samples. For example, if the threshold is determined to be 4.5, then the low slope content is the number of sample points having an absolute slope less than or equal to 4 plus one half of the number of sample points with slope equal to 5.

The spectral width metric, which corresponds to an estimate of the spectral width of the signal for the three-second segment associated with each channel ECG1 and ECG2, is defined, for example, as the difference between the mean frequency and the fundamental frequency of the signal. According to an embodiment of the present invention, the spectral width metric is calculated by determining the difference between the most recent estimate of the RR-cycle length and the mean spectral period of the signal for that channel. As is known in the art, the mean spectral period is the inverse of the mean spectral frequency.

As can be seen in FIG. 5, since noise 506 tends to have a relatively higher spectral width, and normal sinus rhythm 508 tends to have a relatively higher low slope content relative to VF, both noise 506 and normal sinus rhythm 508 would be located outside the VF shock zone 500.

A determination is made for each channel ECG1 and ECG2 as to whether the low slope content for that channel is less than both the first boundary 502 and the spectral width is less than the second boundary 504, i.e., the low slope content is less than −0.0013×spectral width+0.415, and the spectral width is less than 200. For example, once the event is determined to be associated with VF, i.e., the intervals for both channels are determined to be irregular, No in Block 356, a determination is made that channel ECG1 is in the VF shock zone, Yes in Block 360, if, for channel ECG1, both the low slope content is less than the first boundary 502 and the spectral width is less than the second boundary 504. The three second segment for that channel ECG1 is then determined to be shockable, Block 363 and the associated buffer for that channel is updated accordingly. If either the low slope content for the channel is not less than the first boundary 502 or the spectral width is not less than the second boundary, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, both the low slope content is less than the first boundary 502 and the spectral width is less than the second boundary 504. The three second segment for that channel ECG2 is then determined to be shockable, Block 369 and the associated buffer for that channel is updated accordingly. If either the low slope content for the channel is not less than the first boundary 502 or the spectral width is not less than the second boundary, the channel ECG2 is determined not to be in the VF shock zone, No in Block 362, the three second segment for that channel ECG2 is then determined to be not shockable, Block 367, and the associated buffer is updated accordingly.

Figure 6A:
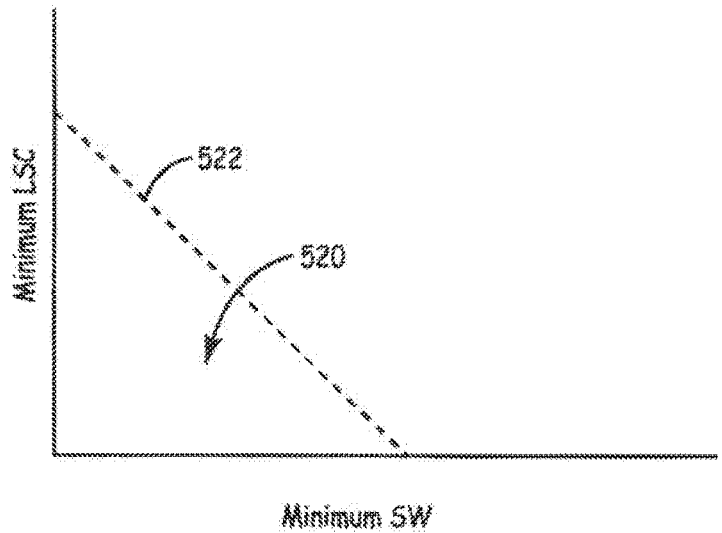
FIGS. 6A and 6B are graphical representations of the determination of whether an event is within a shock zone according to an embodiment of the present invention.
Figure 6B:
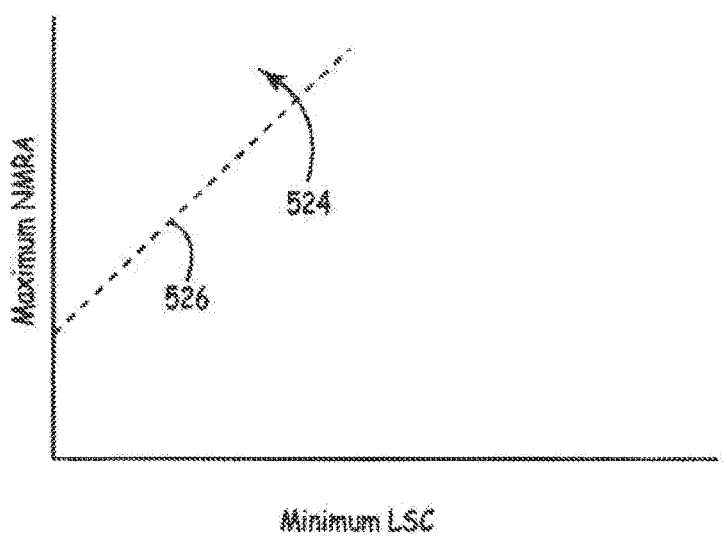

FIGS. 6A and 68 are graphical representations of the determination of whether an event is within a shock zone according to an embodiment of the present invention. During the determination of whether the event is within the VT shock zone, Block 358 of FIG. 4, the low slope content and the spectral width is determined for each channel ECG1 and ECG2, as described above in reference to determining the VF shock zone. A determination is made as to which channel of the two signal channels ECG1 and ECG2 contains the minimum low slope content and which channel of the two signal channels ECG 1 and ECG2 contains the minimum spectral width. A first VT shock zone 520 is defined based on the relationship between the low slope content associated with the channel determined to have the minimum low slope content and the spectral width associated with the channel determined to have the minimum spectral width. For example, according to an embodiment of the present invention, the first VT shock zone 520 is defined by a boundary 522 associated with the minimum low slope content and the minimum spectral width set forth by the equation:

$$LSC = -0.004 \times SW + 0.93 \qquad \text{Equation 1}$$

A second VT shock zone 524 is defined based on the relationship between the low slope content associated with the channel determined to have the minimum low slope content and the normalized mean rectified amplitude associated with the channel determined to have the maximum normalized mean rectified amplitude. In order to determine the normalized mean rectified amplitudes for the two channels ECG1 and ECG2 utilized during the VT shock zone test, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

According to an embodiment of the present invention, for example, the second VT shock zone 524 is defined by a second boundary 526 associated with the relationship between the minimum low slope count and the maximum normalized mean rectified amplitude set forth by the equation:

$$NMRA = 68 \times LSC + 8.16 \qquad \text{Equation 2}$$

If both the minimum low slope count is less than the first boundary 522, i.e., −0.004×minimum spectral width+0.93, and the maximum normalized mean rectified amplitude is greater than the second boundary 526, i.e., 68×minimum low slope count+8.16, the event is determined to be in the VT shock zone, YES in Block 358, and both channels ECG1 and ECG2 are determined to be shockable, Block 357, and the associated buffers are updated accordingly. If either the minimum low slope count is not less than the first boundary 522 or the maximum normalized mean rectified amplitude is not greater than the second boundary 526, the event is determined to be outside the VT shock zone, NO in Block 358, and both channels ECG1 and ECG2 are determined to be not shockable, Block 359.

As described, during both the VF shock zone test, Blocks 360 and 362, and the VT shock zone test, Block 358, the test results for each channel ECG1 and ECG2 as being classified as shockable or not shockable are stored in a rolling buffer containing the most recent eight such designations, for example, for each of the two channels ECG1 and ECG2 that is utilized in the determination of Block 356, as described below.

If only one of the two channels ECG1 and ECG2 is determined to be corrupted by noise, Yes in Block 346, a determination is made whether the signal for the channel not corrupted by noise, i.e., the "clean channel", is more likely associated with a VT event or with a VF event by determining whether the signal for the clean channel includes R-R intervals that are regular and can be therefore classified as being relatively stable, Block 348. If the R-R intervals are determined not to be relatively stable, NO in Block 348, the signal for the clean channel is identified as likely being associated with VF, which is then verified by determining whether the signal for the clean channel is in a VF shock zone, Block 350, described below. If R-R intervals for the clean channel are determined to be stable, YES in Block 348, the signal is identified as likely being associated with VT, which is then verified by determining whether the signal for the clean channel is in a VT shock zone, Block 352.

Figure 7:
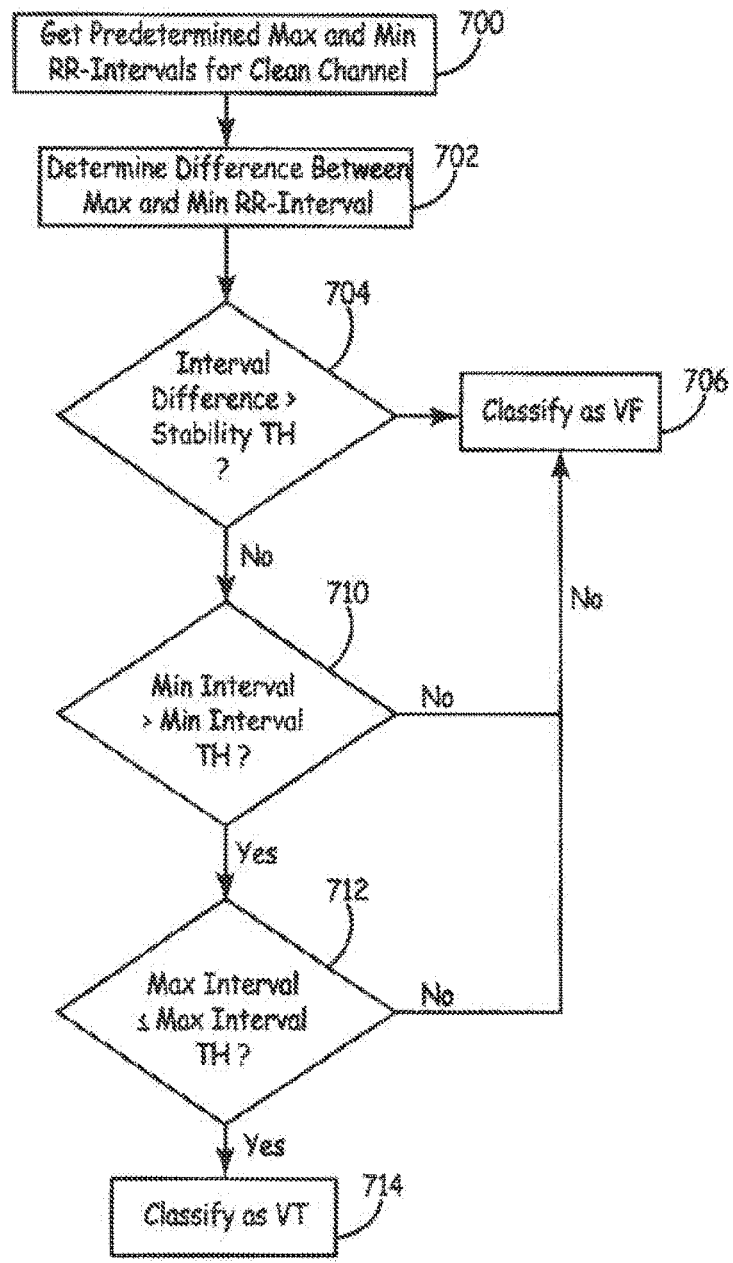
FIG. 7 is a flowchart of a method for discriminating cardiac events according to an embodiment of the disclosure.

According to an embodiment of the present invention, in order to determine whether the signal for the clean channel includes R-R intervals that are regular and the clean channel can be therefore classified as being either relatively stable, Yes in Block 348, or relatively unstable, No in Block 348, the device discriminates VT events from VF events in Block 348 by determining whether the relative level of variation in the RR-intervals associated with the clean channel is regular. FIG. 7 is a flowchart of a method for discriminating cardiac events according to an embodiment of the disclosure. For example, as illustrated in FIG. 7, predetermined maximum and minimum intervals for the clean channel are identified from the updated buffer of 12 RR-intervals, Block 342 of FIG. 4. According to an embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated to generate an interval difference associated with the clean channel, 702. A determination is then made as to whether the interval difference is greater than a predetermined stability threshold, Block 704, such as 110 milliseconds, for example.

If the interval difference is greater than the stability threshold, the event is classified as an unstable event. Block 706, and therefore the clean channel is determined not to include regular intervals, No in Block 348, and a determination is made as to whether the signal associated with the clean channel is within a predetermined VF shock zone. Block 350 of FIG. 4, described below. If the interval difference is less than or equal to the stability threshold, No in Block 704, the device determines whether the minimum RR interval is greater than a minimum interval threshold, Block 710, such as 200 milliseconds, for example.

If the minimum interval is less than or equal to the minimum interval threshold, No in Block 710, the event is classified as an unstable event, Block 706, and therefore the clean channel is determined not to include regular intervals. No in Block 348, and a determination is made as to whether the signal associated with the clean channel is within a predetermined VF shock zone, Block 350 of FIG. 4, described below. If the minimum interval is greater than the minimum interval threshold, Yes in Block 710, the device determines whether the maximum interval is less than or equal to a maximum interval threshold. Block 712, such as 333 milliseconds for example. If the maximum interval is greater than the maximum interval threshold, the event is classified as an unstable event, Block 706, and therefore the clean channel is determined not to include regular intervals. No in Block 348, and a determination is made as to whether the signal associated with the clean channel is within a predetermined VF shock zone, Block 350 of FIG. 4, described below. If the maximum interval is less than or equal to the maximum interval threshold, the event is classified as a stable event, Block 714, and therefore the dean channel is determined to include regular intervals. Yes in Block 348, and a determination is made as to whether the signal associated with the clean channel is within a predetermined VT shock zone, Block 352 of FIG. 4, described below.

Returning to FIG. 4, the determination of whether the clean channel is within the VF shock zone, Block 350, is made based upon a low slope content metric and a spectral width metric, similar to the VF shock zone determination described above in reference to Blocks 360 and 362, both of which are determined for the clean channel using the method described above. Once the low slope content metric and a spectral width metric are determined for the dean channel, the determination of whether the clean channel is in the VF shock zone is made using Equations 1 and 2, so that if either the low slope content for the clean channel is not less than the first boundary 502 or the spectral width is not less than the second boundary 504, the clean channel is determined not to be in the VF zone, No in Block 350 and both channels are classified as not shockable, Block 351, and the associated buffers are updated accordingly.

If the low slope content for the clean channel is less than the first boundary 502 and the spectral width is less than the second boundary 504, the clean channel is determined to be in the VF zone, Yes in Block 350. A determination is then made as to whether the channel determined to be corrupted by noise, i.e., the "noisy channel", is within the VF shock zone, Block 354. If either the low slope content for the noisy channel is not less than the first boundary 502 or the spectral width is not less than the second boundary 504, the noisy channel is determined not to be in the VF zone, No in Block 354, the clean channel is classified as shockable and the noisy channel is classified as not shockable, Block 355, and the associated buffers are updated accordingly.

If the low slope content for the noisy channel is less than the first boundary 502 and the spectral width is less than the second boundary 504, the noisy channel is determined to be in the VF zone. Yes in Block 354, both the clean channel and the noisy channel are classified as being shockable, Block 353, and the associated buffers are updated accordingly.

Similar to the VT shock zone determination described above in reference to Block 358, during the determination as to whether the clean channel is within the VT shock zone in Block 352, the low slope content and the spectral width is determined for the clean channel as described above in reference to determining the VF shock zone. The first VT shock zone 520 is defined based on the relationship between the low slope content and the spectral width associated with the clean channel according to Equation 3, for example, and the second VT shock zone 524 is defined based on the relationship between the low slope count and the normalized mean rectified amplitude associated with the clean channel. The normalized mean rectified amplitudes for the clean channel is the same as described above in reference to the noise detection tests of Block 344. For example, according to an embodiment of the present invention, the second VT shock zone 524 is defined by a second boundary 526 associated with the relationship between the low slope count and the normalized mean rectified amplitude of the clean channel using Equation 2.

If both the low slope count is less than the first boundary 522, i.e., −0.004×spectral width of clean channel+0.93, and the normalized mean rectified amplitude is greater than the second boundary 526, i.e., 68×low slope count of clean channel+8.16, the clean channel is determined to be in the VT shock zone, Yes in Block 352, both channels are classified as being shockable. Block 353, and the associated buffers are updated accordingly.

If either the low slope count is not less than the first boundary 522 or the maximum normalized mean rectified amplitude is not greater than the second boundary 526, the clean channel is determined to be outside the VT shock zone, No in Block 352, both channels are classified as being not shockable, Block 351, and the associated buffers are updated accordingly.

Once the classification of both of the channels ECG1 and ECG2 is made subsequent to the determination of whether the clean channel or channels is in the VT shock zone, Block 352 and 358, or the VF shock zone, Blocks 350 and Blocks 360 and 362 in combination, a determination is made as to whether the device should transition from the concerned state 304 to the armed state 306, Block 370. For example, according to an embodiment of the present invention, the transition from the concerned state 304 to the armed state 306 is confirmed if a predetermined number, such as two out of three for example, of three-second segments for both channels ECG1 and ECG2 have been classified as being shockable. If the predetermined number of three-second segments in both channels ECG1 and ECG2 have been classified as shockable, the device transitions from the concerned state 304 to the armed state 306. Yes in Block 370. If the predetermined number of three-second segments in both channels ECG1 and ECG2 have not been classified as shockable, the device does not transition from the concerned state 304 to the armed state 306, no in Block 370, and a determination as to whether to transition back to the not concerned state 302 is made. Block 372. The determination as to whether to transition from the concerned state 304 back to the not concerned state 302 is made, for example, by determining whether a heart rate estimate is less than a heart rate threshold level in both of the two channels ECG1 and ECG2, using the method for determining a heart rate estimate as described in U.S. Pat. No. 7,894,894 to Stadler et al., incorporated herein by reference in its entirety. If it is determined that the device should not transition to the not concerned state 302, i.e., either of the two heart rate estimates are greater than the heart rate threshold, the process is repeated using the signal generated during a next three-second window. Block 341.

When the device determines to transition from the concerned state 304 to the armed state 306, Yes in Block 370, processing continues to be triggered by a three-second time out as is utilized during the concerned state 304, described above. Prior to making the operating state transition from the concerned state 304 to the armed state, the device performs a state transition rhythm confirmation analysis, Block 373, to confirm the decision to transition from the concerned state to the armed state that was made based on the predetermined number of three-second segments for both channels ECG1 and ECG2 having been classified as being shockable, Block 370.

Figure 8:
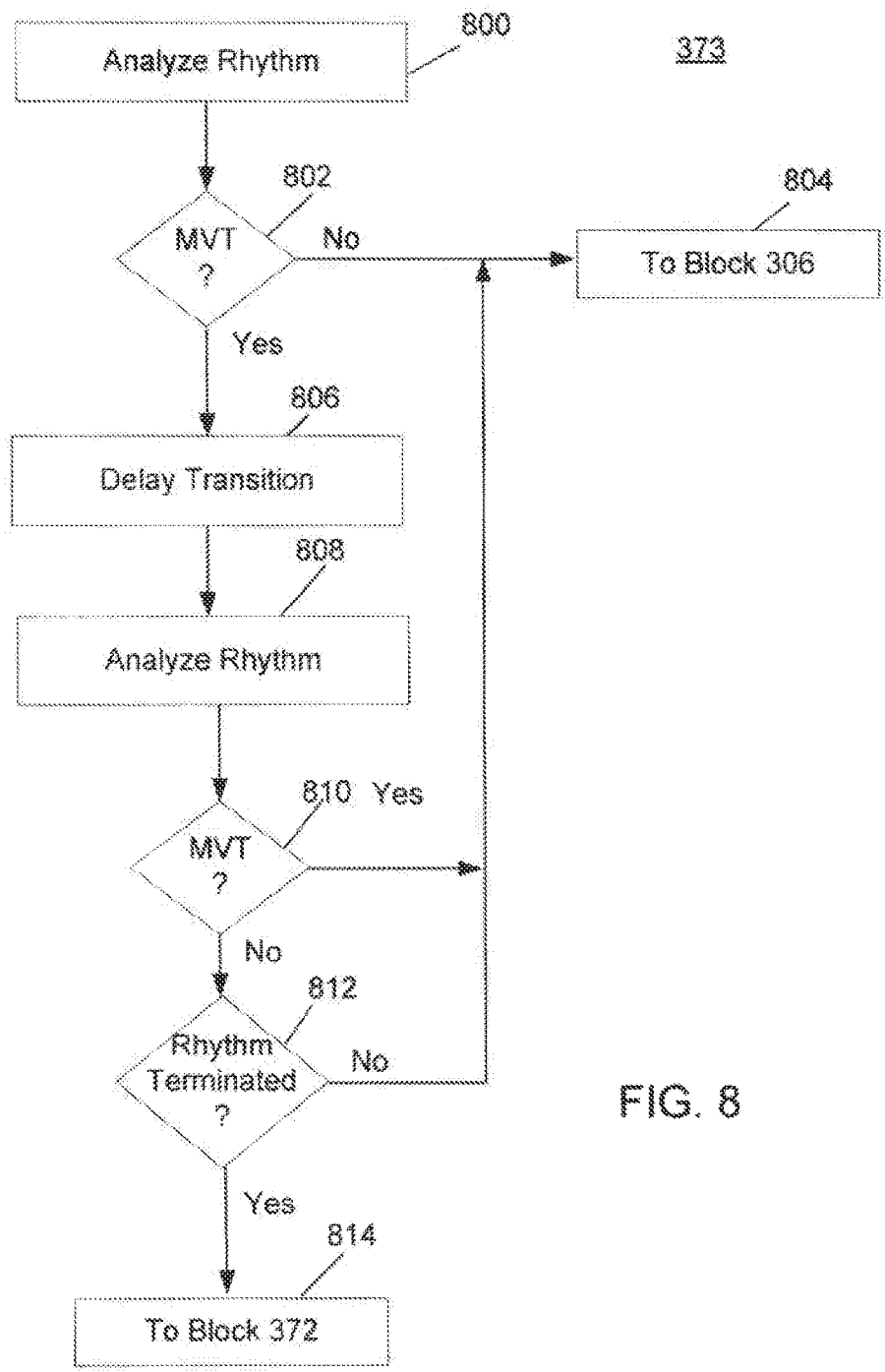
FIG. 8 is a flowchart of a method for determining whether the device is to transition between operating states according to an embodiment of the present invention.

FIG. 8 is a flowchart of a method for determining whether the device is to transition between operating states according to an embodiment of the present invention. For example, as illustrated in FIGS. 4 and 8, during the state transition rhythm confirmation analysis, Block 373, the device analyzes the rhythm associated with the current episode, Block 800, using the three-second windows for both of the sensing channels ECG1 and ECG2 that were previously used in the initial determination of whether to transition to the next operating state, Block 370, prior to the state transition rhythm confirmation analysis. Block 373. During the rhythm analysis, Block 800, the device analyzes the previously detected rhythm to determine whether the rhythm is a monomorphic ventricular tachycardia (MVT) or a polymorphic ventricular tachycardia/fibrillation (PVT).

For example, according to one embodiment, the device analyzes the most recent determined three-second windows that were used to identify the cardiac event as being shockable, Blocks 342-370 of FIG. 4, and for each three-second window associated with sensing channels ECG1 and ECG2, the device compares the morphology of the one of the R-waves in the window with the morphology of the other R-waves in the window. According to one embodiment, for example, the first R-wave is selected, and the comparison is made between each of the subsequent R-waves in the window and the first R-wave. If a predetermined number of the beats in the window match the morphology of the selected beat, the device determines the rhythm to be monomorphic VT for that sensing window. According to an embodiment of the present disclosure, the device determines, for each beat within the window, whether the beat matches the selected beat by a predetermined percentage match. For example, the device determines whether there is a 60 percent or greater match between each beat and the selected beat in the three-second sensing window, and determines the rhythm for the window to be monomorphic VT if all of the subsequent beats are a 60 percent or greater match with the selected beat. According to another embodiment, the device may determine the rhythm for the window to be monomorphic VT if a substantial fraction of the other beats, such as 66 percent or 75 percent, for example, are a 60 percent or greater match with the selected beat. The process is repeated for each of the three-second windows utilized previously to determine whether to transition to the next operating state in Block 370 of FIG. 4. If the rhythm is determined to be a monomorphic VT for each of the previous determined three-second windows, the device determines that the rhythm is a monomorphic VT. Yes in Block 802.

On the other hand, if a predetermined number of the beats in the window do not match the morphology of the selected beat, the device determines the rhythm not to be monomorphic for that sensing window. If either of the three second windows for both of the sensing channels ECG1 and ECG2 are not determined to be monomorphic, the rhythm is not determined to be a monomorphic VT, No in Block 802, and is therefore likely a polymorphic VT/VF. As a result, the rhythm confirmation analysis is aborted and the device transitions from the concerned state 304 to the armed state 306, Block 804, where charging of the capacitor or capacitors is initiated. The operation of the device while in the armed state 306 is described in U.S. Pat. No. 7,894,894 to Stadler et al., incorporated herein by reference in it's entirety.

When the three-second windows of both of the sensing channels ECG1 and ECG2 used previously to determine whether to transition to the next operating state in Block 370 of FIG. 4 are determined to be monomorphic VT, Yes in Block 802, the device delays transitioning from the not concerned state 304 to the concerned state, Block 806. During this operating state transition delay, Block 806, the device waits for the next determination, from Bocks 342-370 of FIG. 4, of whether the sensing channels ECG1 and ECG2 are shockable or not shockable to be performed using one or more of the next three-second windows from the sensing channels ECG1 and ECG2 subsequent to the three-second windows that were used previously in the determination of whether to transition from the concerned operating state 304 to the armed operating state 306, Block 370. Therefore, if two consecutive three-second windows were used in the determination, for example, the delay would be six seconds, and if only one were utilized, the delay would be three-seconds.

Once identified as being monomorphic VT, cardiac rhythms typically tend to subsequently present in one of three ways. The monomorphic VT rhythm may subsequently further deteriorate from being a monomorphic VT rhythm to becoming a polymorphic VT or VF rhythm, may continue presenting as a monomorphic VT rhythm, or may self-terminate shortly after presenting as a monomorphic VT rhythm. Therefore, according to an embodiment of the present disclosure, once the next three-second windows are determined, the device analyzes the newly determined three-second windows. Block 808, by comparing, for each of the current three-second windows ECG1 and ECG2, the morphology of the first R-wave, i.e., the first beat in each newly determined three-second window with the morphology of the subsequent R-waves in the window, as described above in Block 800.

If a predetermined number of the subsequent beats in the window match the morphology of the first beat, the device determines the rhythm to be monomorphic in that sensing window. If the rhythm is determined to be a monomorphic VT for each sensing window: ECG1 and ECG2, the device determines that the rhythm continues to be a monomorphic VT, Yes in Block 810, and therefore the rhythm confirmation analysis is aborted and the device transitions from the concerned state 304 to the armed state 306. Block 804, where charging of the capacitor or capacitors is initiated.

If one or more of the subsequently determined three second windows for both of the sensing channels ECG1 and ECG2 are not determined to be monomorphic, and therefore the cardiac event is likely no longer monomorphic ventricular tachycardia, No in Block 810, the device determines whether the rhythm has terminated. Block 812. According to one embodiment, in order to determine whether the rhythm has terminated in Block 812, the device compares, for each subsequently determined three-second window, the absolute value of each R-wave in the window to a predetermined width threshold. According to one embodiment, the width threshold may be set as approximately 109 milliseconds, for example.

If all of the beats within the sensing window are greater than or equal to the width threshold, the rhythm for that window is determined to be associated with ventricular tachycardia, and therefore, to have not terminated, No in Block 812. If all of the beats within the sensing window are less than the width threshold, the rhythm for that window is determined to be associated with supraventricular tachycardia, and therefore, to have terminated, Yes in Block 812, and the device determines to whether to transition back to the not concerned state 302, Block 372, as described above.

According to another embodiment, in order to determine whether the rhythm has terminated in Block 812, the device compares, for each subsequently determined three-second window, each R-wave within the window with a predetermined sinus rhythm R-wave template to determine a difference between the R-waves and the sinus rhythm R-wave template. If the difference between any one or more of the R-waves within the window is greater than a predetermined difference threshold, such as 39 milliseconds, for example, the rhythm is determined to be a ventricular tachycardia, and therefore to have not terminated, No in Block 812. If the difference between each of the R-waves within the window is less than or equal to the predetermined difference threshold, the rhythm is determined to be a supraventricular tachycardia, and therefore to have terminated, Yes in Block 812.

When the rhythm is determined to no longer be a monomorphic VT and to have not terminated, No in Block 812, the device transitions from the concerned state 304 to the armed state 306, where charging of the capacitor or capacitors is initiated. If the rhythm is determined to no longer be a monomorphic VT and to have terminated, Yes in Block 812, the device determines to whether to transition back to the not concerned state 302, Block 372, as described above, Block 814.

In this way, during the confirmation as to whether to transition from the concerned operating state 304 to the armed operating state 306, Block 373, the device delays charging of the capacitors for the period of time during which one or more of the next three-second windows are utilized to determine whether the rhythm is a monomorphic VT during the subsequent analysis of Blocks 800 and 808.

According to another embodiment, if the rhythm is determined to no longer be a monomorphic VT and to have terminated, Yes in Block 812, the device may automatically adjust the delay period so that during subsequent monomorphic ventricular tachycardia determinations, the delay period is adjusted from it's initial value to another desired value. For example, according to one embodiment, for the initial monomorphic ventricular tachycardia determination in Block 810, the delay may be set as six seconds, i.e., two three-second windows, and if monomorphic ventricular tachycardia is determined to have terminated, YES in Block 812, the device increases the delay from six seconds to nine seconds, i.e., from two to three three-second windows. In addition the delay may be decreased. For example, if the delay is set at nine seconds, and the device determines that the rhythm continues to be monomorphic ventricular tachycardia. YES in Block 810, or to have not terminated, No in Block 812, the device may decrease the delay from nine seconds to six seconds when subsequent determinations are made in Block 810.

According to another embodiment, If one or more of the subsequently determined three second windows for both of the sensing channels ECG1 and ECG2 are not determined to be monomorphic, and therefore the cardiac event is likely no longer monomorphic ventricular tachycardia, No in Block 810, the device does not make the determination as to whether the rhythm has terminated, Block 812. Rather, when the rhythm termination determination. Block 812, is omitted, and it is determined that the cardiac event is likely no longer monomorphic ventricular tachycardia, No in Block 810, the device determines whether to transition back to the not concerned state 302, Block 372, as described above. The determination as to whether the rhythm is no longer a shockable event will be made based on the analysis of the next three-second windows in Blocks 342-370.

Figure 9:
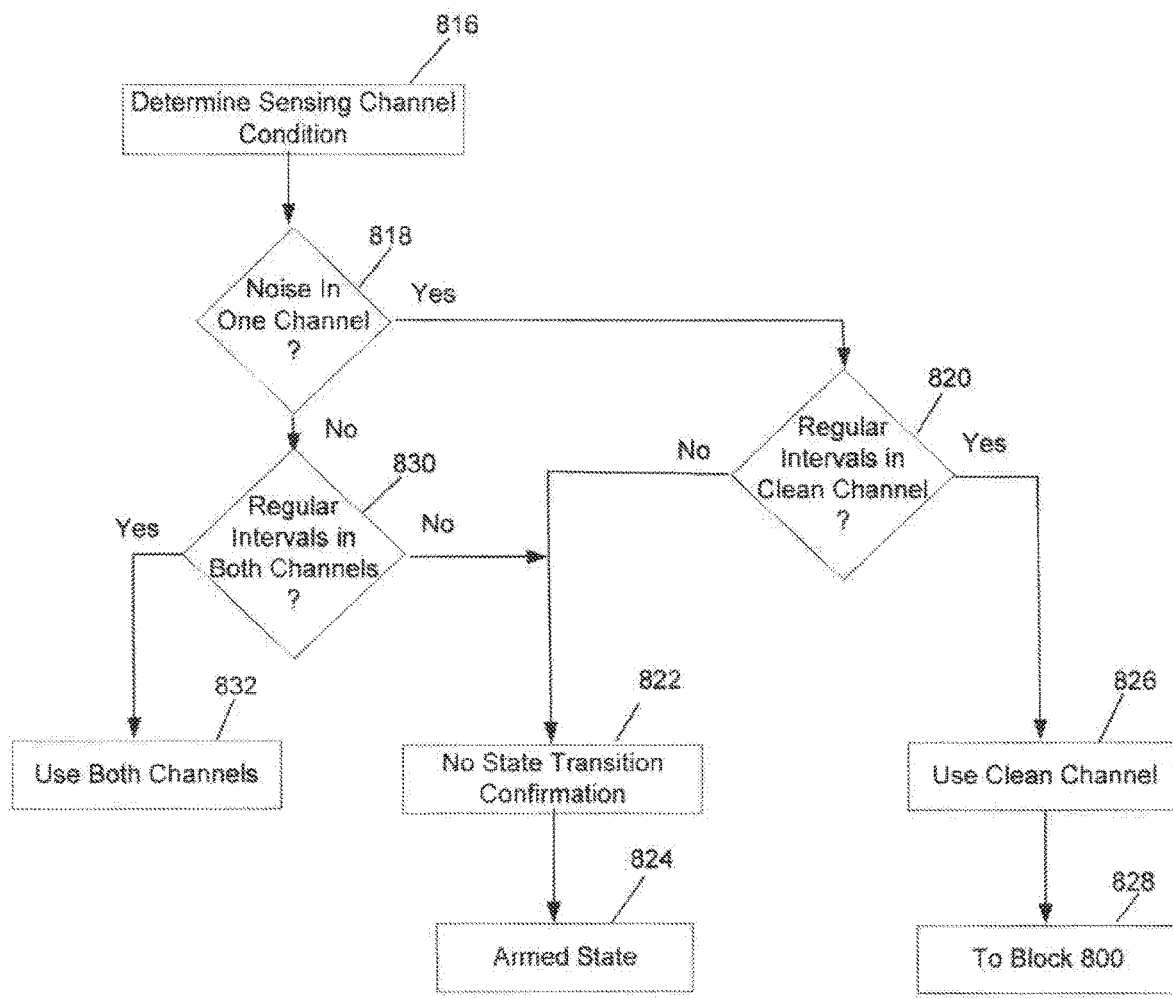
FIG. 9 is a flowchart of a method for determining whether to transition between operating states in a medical device according to an embodiment of the present invention.

FIG. 9 is a flowchart of a method for determining whether to transition between operating states in a medical device according to an embodiment of the present invention. As described above, the device transitions from the concerned operating state 306 to the armed operating state 306, Yes in Block 370 of FIG. 4, when two out of three three-second segments for both channels ECG1 and ECG2 have been classified as being shockable, and performs the state transition rhythm confirmation, Block 373, using the three-second windows for both of the sensing channels ECG1 and ECG2 that were previously used in the initial determination of whether to transition to the next operating state, Block 370, prior to the state transition rhythm confirmation analysis. Block 373.

As can be seen in FIG. 4, how both channels ECG1 and ECG2 could have been determined to be shockable can vary. First, if noise was determined to be occurring in one channel, Yes in Block 346, but the clean channel was determined to have regular intervals, Yes in Block 348, and to be in the VT shock zone, Yes in Block 352, both of the sensing channels ECG1 and ECG2 are determined to be shockable. Block 353. Second, if noise was determined to be occurring in one channel, Yes in Block 346, the clean channel was determined not to have regular intervals, No in Block 348, and both the clean and the noisy channel are determined to be in the VF shock zone, Yes in Blocks 350 and 354, both of the sensing channels ECG1 and ECG2 are determined to be shockable, Block 353.

On the other hand, if noise was not determined to be occurring in either channel, No in Block 346, but both channels are determined to have regular intervals, Yes in Block 356, and both channels are determined to be in the VT shock zone, Yes in Block 358, both of the sensing channels ECG1 and ECG2 are determined to be shockable, Block 359. Finally, if noise was not determined to be occurring in either channel, No in Block 346, but both channels are not determined to have regular intervals, No in Block 356, and both channels are determined to be in the VF shock zone, Yes in Blocks 360 and 362, both of the sensing channels ECG1 and ECG2 are determined to be shockable. Therefore, according to an embodiment of the present disclosure, the device may determine how the three-second windows were determined to be shockable, and based on this determination, decide whether or not to perform the state transition rhythm confirmation, Block 373, and if the confirmation is to be performed, whether one or both of the sensing channels ECG1 and ECG2 are to be used in performing the confirmation.

For example, as illustrated in FIGS. 4, 8 and 9, according to an embodiment of the present disclosure, during the state transition rhythm confirmation, Block 373, the device determines the condition of the sensing channels, ECG1 and ECG2, Block 816, utilized during the initial determination, Blocks 342-370, as to whether the sensing channels ECG1 and ECG2 are shockable or not shockable. For example, the device determines whether noise was determined in one of the sensing channels, ECG1 or ECG2, Block 818. If noise was determined to be occurring in one of the sensing channels. Yes in Block 818, the device determines whether the signal for the clean channel included R-R intervals that were regular and the channel was be therefore classified as being relatively stable, Block 820. If the R-R intervals were determined to not be relatively regular or stable for the dean channel, No in Block 820, the device determines that the state transition rhythm confirmation, Block 373, is not to be performed, Block 822, and that the transition to the armed state 306 should be initiated without delay, Block 824. If the R-R intervals were determined to be relatively regular or stable. Yes in Block 820, the device determines that the state transition rhythm confirmation, Block 373, is to be performed and that the clean channel only is to be utilized, Block 826, in the confirmation, Block 828, as described below.

If noise was not determined to be occurring one of the sensing channels, i.e., both sensing channels were dean, Yes in Block 818, the device determines whether the signal for both channels included R-R intervals that were regular and the channel was be therefore classified as being relatively stable, Block 830. If the R-R intervals were determined to not be relatively regular or stable for both channels, No in Block 830, the device determines that the state transition rhythm confirmation, Block 373, is not to be performed, Block 822, and that the transition to the armed state 306 should be initiated without delay, Block 824. If the R-R intervals were determined to be relatively regular or stable for both channels, Yes in Block 830, the device determines that the state transition rhythm confirmation, Block 373, is to be performed and that both channels are to be utilized, Block 832, in the confirmation, Block 828, as described above.

If only the single clean channel is determined to be utilized in the confirmation, Block 828, the device analyzes the rhythm associated with the current episode, Block 800, using the three-second windows for the only the dean sensing channel ECG1 or ECG2 used during the initial determination of whether to transition to the next operating state. Block 370, prior to the state transition rhythm confirmation analysis. Block 373. During the rhythm analysis, Block 800, the device analyzes the previously detected rhythm in the clean sensing channel ECG1 or ECG2 to determine whether the rhythm is a monomorphic ventricular tachycardia (MVT) or a polymorphic ventricular tachycardia/fibrillation (PVT).

For example, according to one embodiment, the device analyses the most recent determined three second windows, and for each clean three-second window ECG1 or ECG2, compares the morphology of the first R-wave, i.e., the first beat, in the window with the morphology of the subsequent R-waves in the window. If a predetermined number of the subsequent beats in the window match the morphology of the first beat, the device determines the rhythm to be monomorphic for that sensing window. If the rhythm is determined to be a monomorphic VT for the clean sensing window, ECG1 or ECG2, the device determines that the rhythm is a monomorphic VT, Yes in Block 802.

On the other hand, if the three second windows for the dean sensing channel ECG1 or ECG2 is not determined to be monomorphic, NO in Block 802, the rhythm is not determined to be a monomorphic VT, No in Block 802, and is therefore likely a polymorphic VT/VF. Therefore, rhythm confirmation analysis is aborted and the device transitions from the concerned state 304 to the armed state 306, Block 804, where charging of the capacitor or capacitors is initiated. The operation of the device while in the armed state 306 is described in U.S. Pat. No. 7,894,894 to Stadler et al., incorporated herein by reference in its entirety.

When the three second windows of the clean sensing channel ECG1 or ECG2 is determined to be monomorphic VT, Yes in Block 802, the device delays transitioning from the not concerned state 304 to the concerned state, Block 806. During this operating state transition delay. Block 806, the device waits for the next determination, from Bocks 342-370 of FIG. 4, of whether the sensing channels ECG1 and ECG2 are shockable or not shockable to be performed using the next three-second windows from the sensing channels ECG1 and ECG2 subsequent to the three-second windows that were already used previously in the determination of whether to transition from the concerned operating state 304 to the armed operating state 306, Block 370.

As described above, the device analyzes the newly determined three-second windows, Block 808, by comparing, for the current three-second window of the clean channel ECG1 or ECG2, the morphology of the first R-wave, i.e., the first beat in each newly determined three-second window for the clean sensing channel with the morphology of the subsequent R-waves in the window.

If a predetermined number of the subsequent beats in the window match the morphology of the first beat, the device determines the rhythm to be monomorphic in that sensing window. If the rhythm is determined to be a monomorphic VT for each sensing window, ECG1 and ECG2, the device determines that the rhythm is continues to be a monomorphic VT, Yes in Block 810, and therefore the rhythm confirmation analysis is aborted and the device transitions from the concerned state 304 to the armed state 306, Block 804, where charging of the capacitor or capacitors is initiated.

If the subsequently determined three second window for the clean sensing channel ECG1 or ECG2 is not determined to be monomorphic. NO in Block 810, the device determines whether the rhythm has terminated, Block 812, as described below. If the rhythm is determined to no longer be a monomorphic VT and to have not terminated, No in Block 812, the device transitions from the concerned state 304 to the armed state 306, where charging of the capacitor or capacitors is initiated. If the rhythm is determined to no longer be a monomorphic VT and to have terminated, Yes in Block 812, the device determines to whether to transition back to the not concerned state 302, Block 372, as described above.

Figure 10:
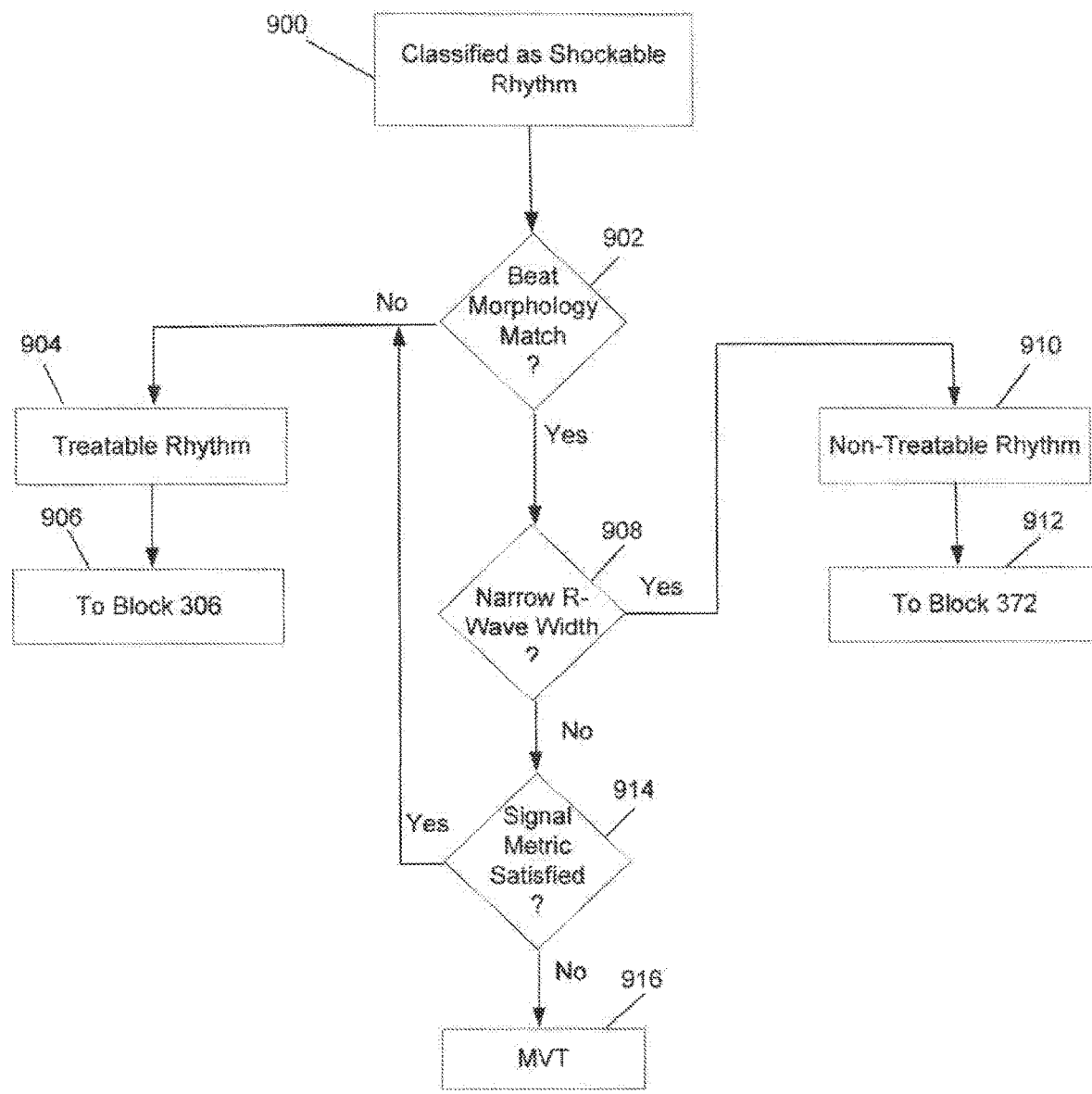
FIG. 10 is a flowchart of a method for discriminating a cardiac event according to an embodiment of the present disclosure.

FIG. 10 is a flowchart of a method for discriminating a cardiac event according to an embodiment of the present disclosure. According to an embodiment of the present disclosure, the device may use one or more rhythm discrimination thresholds to further discriminate the rhythm during the rhythm analysis in one or both of Blocks 800 and 808 as being either monomorphic, polymorphic or normal sinus rhythm. For example, as illustrated in FIG. 10, once the rhythm is classified as being shockable in Blocks 342-370 of FIG. 4, Block 900, the device compares the R-waves in the previously determined three-second windows used in determining to transition from the concerned operating state 304 to the armed operating state 306 to generate a template match score for each of the R-waves in the window. A determination is made for each sensing vector as to whether the match scores for the interval of the sensing vector exceed a predetermined match score threshold.

For example, the device compares the morphology of the one of the R-waves in the window with the morphology of the other R-waves in the window. According to one embodiment, for example, the first R-wave is selected as the template, and the comparison is made between each of the subsequent R-waves in the window and the first R-wave. If a predetermined number of the beats in the window match the morphology of the selected beat, the device determines the rhythm to be monomorphic for that sensing window.

According to an embodiment of the present disclosure, the device determines, for each beat within the window, whether the beat matches the selected beat by a predetermined percentage match. For example, according to one embodiment, the device determines whether there is a 60 percent or greater match between each beat and the selected beat in the three-second sensing window, and determines the rhythm for the window to be monomorphic VT if all of the subsequent beats are a 60 percent or greater match with the selected beat. According to another embodiment, the device may determine the rhythm for the window to be monomorphic VT if a substantial fraction of the other beats, such as 66 percent or 75 percent, for example, are a 60 percent or greater match with the selected beat. The process is repeated for each of the three-second windows utilized previously to determine whether to transition to the next operating state in Block 370 of FIG. 4.

If the predetermined number of the match scores are not determined to be within the match score range for both sensing vectors if two are being utilized, or for the one sensing vector if only one sensing vector is being utilized, and so forth, the VT morphology match is determined not to be satisfied, No in Block 902, and the rhythm is therefore determined to likely be associated with a treatable rhythm, such as polymorphic VT, ventricular fibrillation or ventricular flutter, Block 904. As a result, the rhythm confirmation analysis is aborted and the device transitions from the concerned state 304 to the armed state 306, Block 906, where charging of the capacitor or capacitors is initiated, as described above.

If all of the subsequent beats match the selected beat by a predetermined percentage match threshold and therefore the rhythm is determined to be monomorphic for each of the previous determined three-second windows, the device determines that the rhythm is a monomorphic rhythm, Yes in Block 902. However, because a monomorphic rhythm could be either sinus tachycardia/supraventricular tachycardia, monomorphic ventricular tachycardia, or ventricular flutter, in order to further distinguish the a monomorphic rhythm, the device determines, for each window, whether a predetermined number of R-wave widths associated with the beats in each of the three-second windows is within a predetermined range reflective of a given cardiac rhythm, Block 908. For example, according to an embodiment of the present disclosure, the device compares, for each three-second window, the absolute value of each R-wave in the window to a predetermined R-wave width threshold. According to one embodiment, the width threshold may be set as approximately 109 milliseconds, for example, and the device determines whether all of the beats within the window are less than the width threshold.

If the predetermined number of beats within the sensing window are less the width threshold, the R-wave width threshold for that window is determined to be satisfied. On the other hand, if the predetermined number of beats within the sensing window are not less than the width threshold, the R-wave width threshold for that window is determined not to be satisfied.

The process is repeated for all of the three-second windows being utilized in the rhythm confirmation analysis, and if the R-wave width threshold is determined to be satisfied for each three-second window. Yes in Block 908, the monomorphic rhythm is therefore determined to likely be associated with a normal rhythm not requiring shock therapy, such as normal sinus rhythm, sinus tachycardia, or supraventricular tachycardia, Block 910. As a result, the rhythm confirmation analysis is completed and the device determines to whether to transition back to the not concerned state 302, Block 372 of FIG. 4: as described above, Block 912.

If the R-wave width threshold is determined to not be satisfied for one or more of the three-second windows, and therefore the R-wave width threshold is determined not to be satisfied, No in Block 908, the monomorphic rhythm determined to be associated with either monomorphic ventricular tachycardia or ventricular flutter. Since a rhythm associated with ventricular flutter is typically more sinusoidal than a rhythm associated with monomorphic ventricular tachycardia, in order to further distinguish between the rhythm as being either monomorphic ventricular tachycardia or ventricular flutter, the device determines whether a monomorphic signal metric for indicating the cardiac event as being a sinusoidal event is satisfied, Block 914. In order to determine whether a monomorphic signal metric is satisfied, the device determines, for each three-second window utilized, whether the signal for the window satisfies the monomorphic signal metric.

According to one embodiment, the determination of whether the monomorphic signal metric is satisfied is made using a determined low slope content metric in combination with a determined normalized mean rectified amplitude for each relevant three-second window. The low slope content metric may be calculated as the ratio of the number of data points with low slope to the total number of samples in the 3-second segment. For example, according to an embodiment of the present invention, the difference between successive ECG samples is determined as an approximation of the first derivative (i.e, the slope) of the ECG signal. In particular, the raw signal for each channel is applied to a first order derivative filter to obtain a derivative signal for the three-second segment. The derivative signal is then rectified, divided into four equal sub-segments, and the largest absolute slope is estimated for each of the four sub-segments.

A determination is made as to whether the largest absolute slopes are less than a portion of the overall largest absolute slope for the whole three-second segment, such as one-fifth of the overall absolute slope, for example. If the largest absolute slope is less than the portion of the overall slope, then the slope value for that sub-segment is set equal to the overall largest absolute slope. If the largest absolute slope is not less than the portion of the overall slope, then the slope value for that sub-segment is set equal to the determined largest absolute slope for the sub-segment.

Once the slope value for each of the sub-segments has been determined and updated by being set equal to the largest slope for the three second segment, if necessary, the average of the four slopes is calculated and divided by a predetermined factor, such as 16 for example, to obtain a low slope threshold. The low slope content is then obtained by determining the number of sample points in the three-second segment having an absolute slope less than or equal to the low slope threshold.

According to an embodiment of the present invention, if, during the determination of the low slope threshold, the low slope threshold is a fraction, rather than a whole number, a correction is made to the low slope content to add a corresponding fraction of the samples. For example, if the threshold is determined to be 4.5, then the low slope content is the number of sample points having an absolute slope less than or equal to 4 plus one half of the number of sample points with slope equal to 5.

In order to determine the normalized mean rectified amplitudes for the two channels ECG1 and ECG2 utilized during the determination of the morphology signal metric, the amplitude of each R-wave associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

The determined low slope content for each utilized sensing window is compared to a low slope content threshold, such as 0.2, for example, and the determined normalized mean rectified amplitude is compared to an amplitude threshold, such as 60 for example. If both the low slope content is less than the low slope content threshold and the normalized mean rectified amplitude is greater than the amplitude threshold, the morphology metric is determined to be satisfied for that sensing window.

If one or more of the rhythms for the three-second windows are determined to not satisfy the monomorphic signal metric, the cardiac event is determined not to satisfy the monomorphic signal metric, No in Block 914, and the cardiac event is determined to be a non-terminating monomorphic VT rhythm, Block 916. If all of the rhythms for the three-second windows are determined to satisfy the monomorphic signal metric, the cardiac event is determined to satisfy the monomorphic signal metric, Yes in Block 914, the cardiac event is determined to be ventricular flutter, Block 904, and as a result, the rhythm confirmation analysis is aborted and the device transitions from the concerned state 304 to the armed state 306, Block 906, where charging of the capacitor or capacitors is initiated, as described above.

Figure 11:
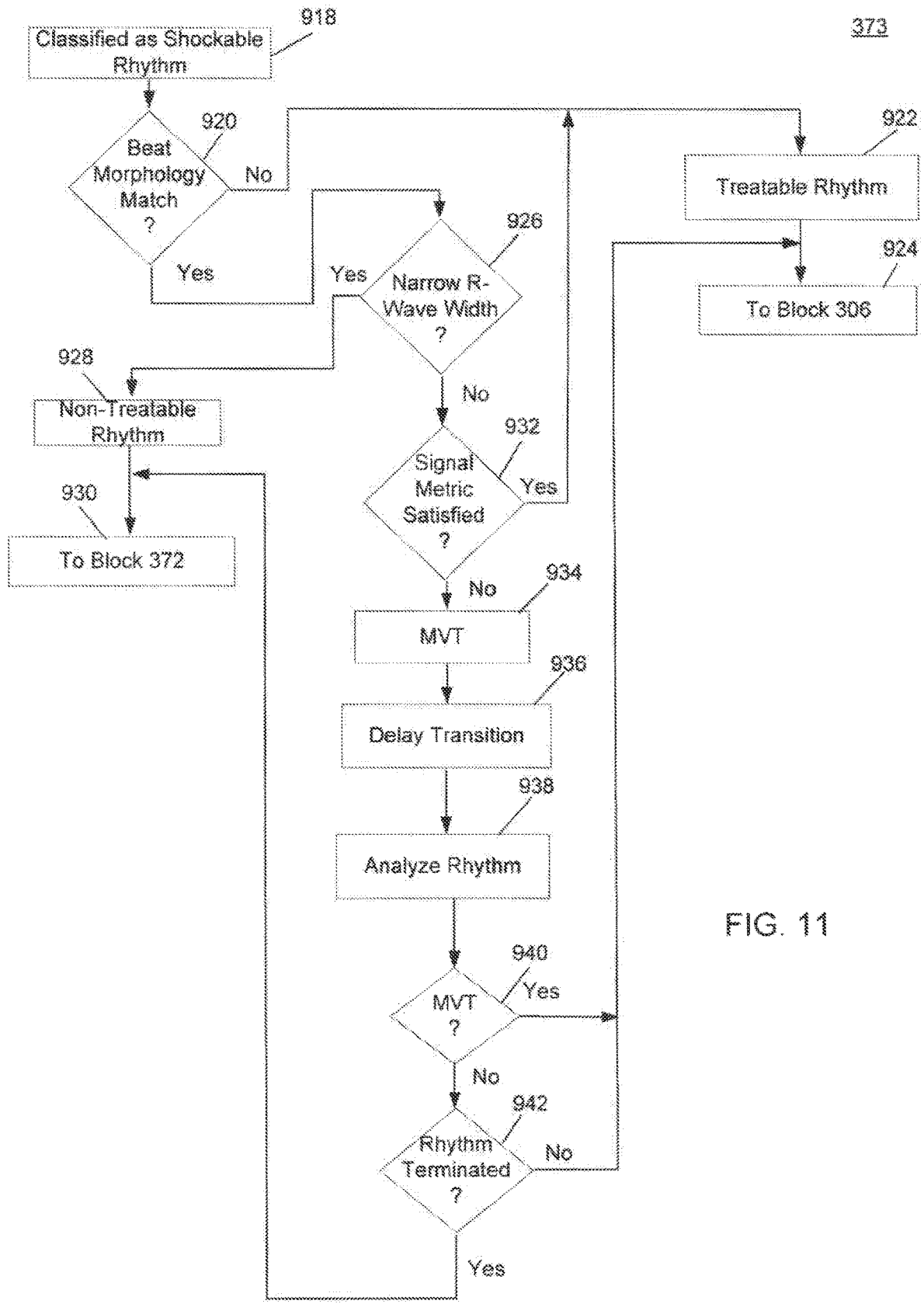
FIG. 11 is a flowchart of a method for determining whether the device is to transition between operating states according to an embodiment of the present invention.

FIG. 11 is a flowchart of a method for determining whether the device is to transition between operating states according to an embodiment of the present invention. According to an embodiment of the present disclosure, the additional discrimination of FIG. 10 may be utilized during the initial rhythm analysis Block 800 of the state transition rhythm confirmation Block 373. For example, as illustrated in FIG. 11, once the rhythm is classified as being shockable in Blocks 342-370 of FIG. 4, Block 918, the device compares the R-waves in the previously determined three-second windows used in determining to transition from the concerned operating state 304 to the armed operating state 306 to generate a template match score for each of the R-waves in the window. A determination is made for each sensing vector as to whether the match scores for the interval of the sensing vector exceed a predetermined match score threshold.

For example, the device compares the morphology of the one of the R-waves in the window with the morphology of the other R-waves in the window. According to one embodiment, for example, the first R-wave is selected as the template, and the comparison is made between each of the subsequent R-waves in the window and the first R-wave. If a predetermined number of the beats in the window match the morphology of the selected beat, the device determines the rhythm to be monomorphic for that sensing window.

According to an embodiment of the present disclosure, the device determines, for each beat within the window, whether the beat matches the selected beat by a predetermined percentage match. For example, according to one embodiment, the device determines whether there is a 60 percent or greater match between each beat and the selected beat in the three-second sensing window, and determines the rhythm for the window to be monomorphic VT if all of the subsequent beats are a 60 percent or greater match with the selected beat. According to another embodiment, the device may determine the rhythm for the window to be monomorphic VT if a substantial fraction of the other beats, such as 66 percent or 75 percent, for example, are a 60 percent or greater match with the selected beat. The process is repeated for each of the three-second windows utilized previously to determine whether to transition to the next operating state in Block 370 of FIG. 4.

If the predetermined number of the match scores are not determined to be within the match score range for both sensing vectors if two are being utilized, or for the one sensing vector if only one sensing vector is being utilized, and so forth, the VT morphology match is determined not to be satisfied, No in Block 920, and the rhythm is therefore determined to likely be associated with a treatable rhythm, such as polymorphic VT, ventricular fibrillation or ventricular flutter, Block 904. As a result, the rhythm confirmation analysis is aborted and the device transitions from the concerned state 304 to the armed state 306, Block 906, where charging of the capacitor or capacitors is initiated, as described above.

If all of the subsequent beats match the selected beat by a predetermined percentage match threshold and therefore the rhythm is determined to be monomorphic for each of the previous determined three-second windows, the device determines that the rhythm is a monomorphic rhythm, Yes in Block 920. However, because a monomorphic rhythm could be either sinus tachycardia/supraventricular tachycardia, monomorphic ventricular tachycardia, or ventricular flutter, in order to further distinguish the a monomorphic rhythm, the device determines, for each window, whether a predetermined number of R-wave widths associated with the beats in each of the three-second windows is within a predetermined range reflective of a given cardiac rhythm, Block 926. For example, according to an embodiment of the present disclosure, the device compares, for each three-second window, the absolute value of each R-wave in the window to a predetermined R-wave width threshold. According to one embodiment, the width threshold may be set as approximately 109 milliseconds, for example, and the device determines whether all of the beats within the window are less than the width threshold.

If the predetermined number of beats within the sensing window are less the width threshold, the R-wave width threshold for that window is determined to be satisfied. On the other hand, if the predetermined number of beats within the sensing window are not less than the width threshold, the R-wave width threshold for that window is determined not to be satisfied.

The process is repeated for all of the three-second windows being utilized in the rhythm confirmation analysis, and if the R-wave width threshold is determined to be satisfied for each three-second window, Yes in Block 926, the monomorphic rhythm is therefore determined to likely be associated with a normal rhythm not requiring shock therapy, such as normal sinus rhythm, sinus tachycardia, or supraventricular tachycardia, Block 928. As a result, the rhythm confirmation analysis is completed and the device determines to whether to transition back to the not concerned state 302, Block 372 of FIG. 4, as described above, Block 930.

If the R-wave width threshold is determined to not be satisfied for one or more of the three-second windows, and therefore the R-wave width threshold is determined not to be satisfied, No in Block 926, the monomorphic rhythm is determined to be associated with either monomorphic ventricular tachycardia or ventricular flutter. Since a rhythm associated with ventricular flutter is typically more sinusoidal than a rhythm associated with monomorphic ventricular tachycardia, in order to further distinguish between the rhythm as being either monomorphic ventricular tachycardia or ventricular flutter, the device determines whether a monomorphic signal metric for indicating the cardiac event as being a sinusoidal event is satisfied. Block 932. In order to determine whether a monomorphic signal metric is satisfied, the device determines, for each three-second window utilized, whether the signal for the window satisfies the monomorphic signal metric, as described above.

If all of the rhythms for the three-second windows are determined to satisfy the monomorphic signal metric, the cardiac event is determined to satisfy the monomorphic signal metric, Yes in Block 932, the cardiac event is determined to be ventricular flutter, which is a treatable rhythm, Block 922, and as a result, the rhythm confirmation analysis is aborted and the device transitions from the concerned state 304 to the armed state 306, Block 924, where charging of the capacitor or capacitors is initiated, as described above. If one or more of the rhythms for the three-second windows are determined to not satisfy the monomorphic signal metric, the cardiac event is determined not to satisfy the monomorphic signal metric, No in Block 932, and the cardiac event is determined to be a non-terminating monomorphic VT rhythm. Block 934.

Once the event is determined to be a monomorphic ventricular tachycardia rhythm, Block 934, the device delays transitioning from the not concerned state 304 to the concerned state, Block 936, as described above. During this operating state transition delay. Block 936, the device waits for the next determination, from Bocks 342-370 of FIG. 4, of whether the sensing channels ECG1 and ECG2 are shockable or not shockable to be performed using the next three-second windows from the sensing channels ECG1 and ECG2 subsequent to the three-second windows that were used previously in the determination of whether to transition from the concerned operating state 304 to the armed operating state 306, Block 370.

Once the next determination of whether the sensing channels ECG1 and ECG2 are shockable or not shockable is completed, the device analyzes the newly determined three-second windows, Block 938, by comparing, for each of the current three-second windows ECG1 and ECG2, the morphology of the first R-wave, i.e., the first beat in each newly determined three-second window with the morphology of the subsequent R-waves in the window, as described above in Block 800.

If a predetermined number of the subsequent beats in the window match the morphology of the first beat, the device determines the rhythm to be monomorphic in that sensing window. If the rhythm is determined to be a monomorphic VT for each sensing window, ECG1 and ECG2, the device determines that the rhythm continues to be a monomorphic VT, Yes in Block 940, and therefore the rhythm confirmation analysis is aborted and the device transitions from the concerned state 304 to the armed state 306, Block 924, where charging of the capacitor or capacitors is initiated.

If one or more of the subsequently determined three second windows for both of the sensing channels ECG1 and ECG2 are not determined to be monomorphic, NO in Block 940, the device may determine whether the rhythm has terminated, Block 942. According to one embodiment, in order to determine whether the rhythm has terminated in Block 942, the device compares, for each subsequently determined three-second window, the absolute value of each R-wave in the window to a predetermined width threshold. According to one embodiment, the width threshold may be set as approximately 109 milliseconds, for example.

If all of the beats within the sensing window are greater than or equal to the width threshold, the rhythm for that window is determined to be associated with ventricular tachycardia, and therefore, to have not terminated, No in Block 942. If all of the beats within the sensing window are less than the width threshold, the rhythm for that window is determined to be associated with supraventricular tachycardia, and therefore, to have terminated, Yes in Block 942, and the device determines to whether to transition back to the not concerned state 302, Block 372, as described above. Block 930.

Figure 12:
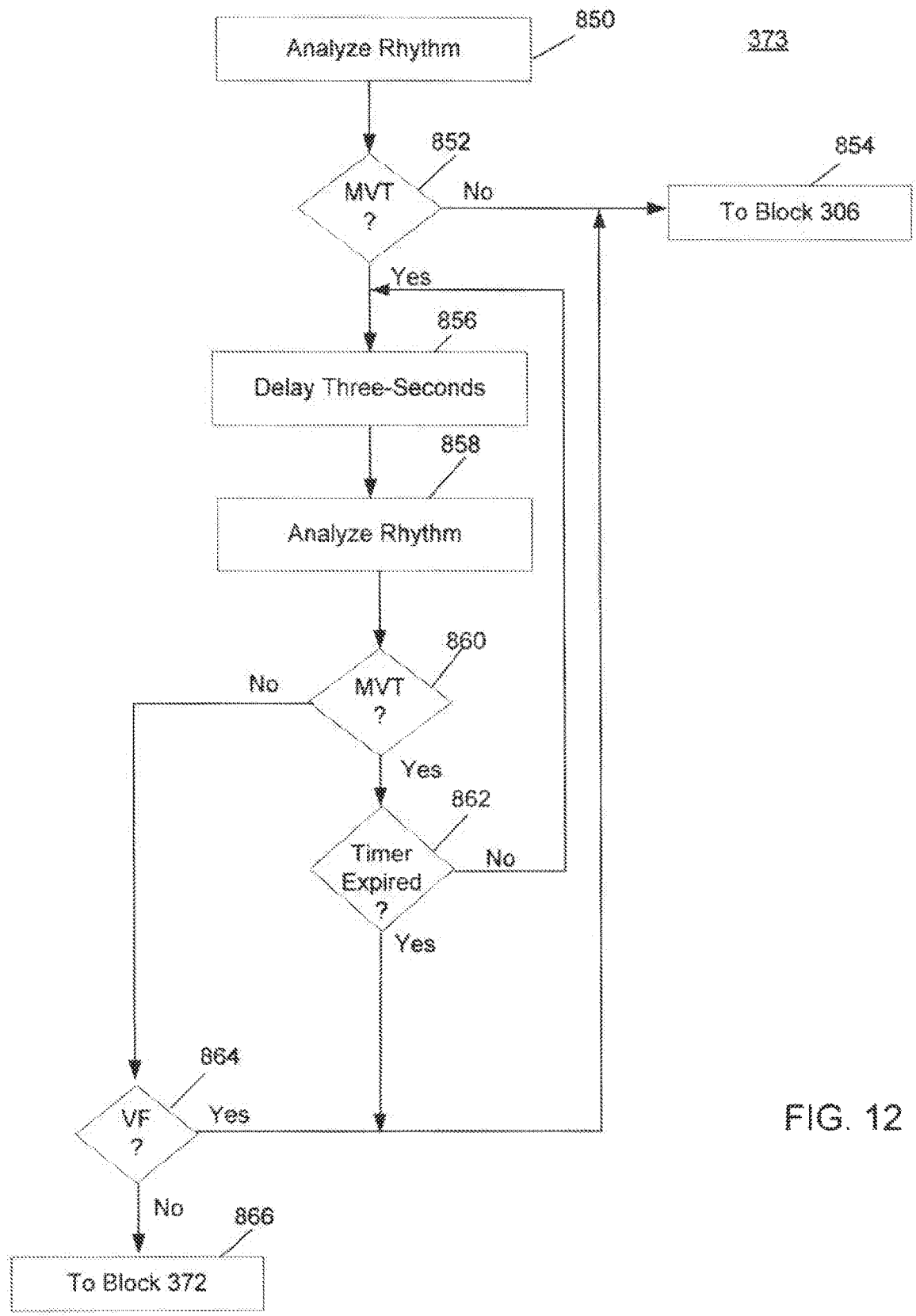
FIG. 12 is a flowchart of a method for determining whether the device is to transition between operating states according to an embodiment of the present invention.

FIG. 12 is flowchart of a method for determining whether the device is to transition between operating states according to an embodiment of the present invention. According to an embodiment, as illustrated in FIGS. 4 and 12, during the state transition rhythm confirmation analysis, Block 373, the device analyzes the rhythm associated with the current episode, Block 850, using the three-second windows for both of the sensing channels ECG1 and ECG2 that were previously used in the initial determination of whether to transition to the next operating state, Block 370, prior to the state transition rhythm confirmation analysis, Block 373. During the rhythm analysis, Block 850, the device analyzes the previously detected rhythm to determine whether the rhythm is a monomorphic ventricular tachycardia (MVT) or a polymorphic ventricular tachycardia/fibrillation (PVT).

For example, according to one embodiment, the device analyzes the most recent determined three-second windows that were used to identify the cardiac event as being shockable, Blocks 342-370 of FIG. 4, and for each three-second window associated with sensing channels ECG1 and ECG2, the device compares the morphology of the one of the R-waves in the window with the morphology of the other R-waves in the window. According to one embodiment, for example, the first R-wave is selected, and the comparison is made between each of the subsequent R-waves in the window and the first R-wave. If a predetermined number of the beats in the window match the morphology of the selected beat, the device determines the rhythm to be monomorphic VT for that sensing window.

According to an embodiment of the present disclosure, the device determines, for each beat within the window, whether the beat matches the selected beat by a predetermined percentage match. For example, the device determines whether there is a 60 percent or greater match between each beat and the selected beat in the three-second sensing window, and determines the rhythm for the window to be monomorphic VT if all of the subsequent beats are a 60 percent or greater match with the selected beat. According to another embodiment, the device may determine the rhythm for the window to be monomorphic VT if a substantial fraction of the other beats, such as 66 percent or 75 percent, for example, are a 60 percent or greater match with the selected beat. The process is repeated for each of the three-second windows utilized previously to determine whether to transition to the next operating state in Block 370 of FIG. 4. If the rhythm is determined to be a monomorphic VT for each of the previous determined three-second windows, the device determines that the rhythm is a monomorphic VT, Yes in Block 852.

On the other hand, if a predetermined number of the beats in the window do not match the morphology of the selected beat, the device determines the rhythm not to be monomorphic for that sensing window. If either of the three second windows for both of the sensing channels ECG1 and ECG2 are not determined to be monomorphic, the rhythm is not determined to be a monomorphic VT, No in Block 852, and is therefore likely a polymorphic VT/VF. As a result, the rhythm confirmation analysis is aborted and the device transitions from the concerned state 304 to the armed state 306, Block 854, where charging of the capacitor or capacitors is initiated. The operation of the device while in the armed state 306 is described in U.S. Pat. No. 7,894,894 to Stadler et al., incorporated herein by reference in it's entirety.

When the three-second windows of both of the sensing channels ECG1 and ECG2 used previously to determine whether to transition to the next operating state in Block 370 of FIG. 4 are determined to be monomorphic VT, Yes in Block 852, the device delays transitioning from the not concerned state 304 to the concerned state. Block 856 for three seconds. During this operating state transition delay, Block 856, the device waits for the next determination, from Bocks 342-370 of FIG. 4, of whether the sensing channels ECG1 and ECG2 are shockable or not shockable to be performed using the next two simultaneous three-second windows from the sensing channels ECG1 and ECG2 subsequent to the three-second windows that were used previously in the determination of whether to transition from the concerned operating state 304 to the armed operating state 306, Block 370.

The device analyzes the newly determined three-second window, Block 858, by comparing a selected R-wave in the newly simultaneously determined three-second windows ECG1 and ECG 2 with the morphology of the other R-waves in the window, as described above, to determine, for each of the two simultaneously sensed windows, whether the three-second window is associated with monomorphic ventricular tachycardia, Block 860.

If a predetermined number of the beats in the window do match the morphology of the selected beat, the rhythm for the three-second window containing the beats is determined to be monomorphic VT. On the other hand, if a predetermined number of the beats in the window do not match the morphology of the selected beat, the rhythm for the three-second window containing the beats is determined not to be monomorphic VT. If one or both of the simultaneous three-second sensing windows ECG1 and ECG2 are determined not to be monomorphic VT, the device determines the rhythm to no longer be monomorphic VT, No in Block 860. A determination is then made as to whether the rhythm is a ventricular fibrillation, Block 864.

According to an embodiment, the device may determine whether the rhythm is ventricular fibrillation in Block 864 using the programmed tachycardia threshold of the device, such as whether the rate associated with the rhythm is greater than 240 beats per minute, for example. According to another embodiment, the device may determine whether the rhythm is ventricular fibrillation in Block 864 by determining whether the rhythm has increased by a predetermined rate, such as 30 beats per minute, for example, from the prior rate of the established monomorphic ventricular tachycardia. If the rhythm determined is to be ventricular fibrillation, Yes in Block 864, the device transitions from the concerned state 304 to the armed state 306, Block 804, where charging of the capacitor or capacitors is initiated. If the rhythm is not determined to be ventricular fibrillation, No in Block 864, the device determines to whether to transition back to the not concerned state 302, Block 372, as described above, Block 866.

If both of the simultaneous three-second sensing windows ECG1 and ECG2 are determined to be monomorphic VT, the device determines the rhythm to continue to be monomorphic VT for those three-second windows, Yes in Block 860. A determination is then made as to whether the total delay period has terminated by determining whether a timer has expired, Block 862. For example, if the operating state transition delay Block 373 is to be performed for the next two simultaneously determined three-second windows, the total delay would be six seconds. Therefore, if six seconds have not expired since initiation of the operating state transition delay, No in Block 862, meaning that the shockable or not shockable determination, Blocks 342-370 of FIG. 4, has only been determined for the first two simultaneous sensings in the two sensing channels ECG 1 and ECG 2, the device waits for the shockable or not shockable determination, Blocks 342-370 of FIG. 4, to be completed for the subsequent two simultaneous sensings in the two sensing channels ECG1 and ECG 2, so that the delay process, Blocks 858-866, is then repeated for the next determined three-second windows.

If the rhythm is no longer monomorphic ventricular tachycardia for the subsequent simultaneously determined three-second windows associated with the two sensing channels ECG 1 and ECG 2, No in Block 860, the determination as to whether the rhythm is ventricular fibrillation, Block 864, is repeated for the subsequent simultaneously determined three-second windows. If the subsequent rhythm is determined to be ventricular fibrillation, Yes in Block 864, the device transitions from the concerned state 304 to the armed state 306. Block 804, where charging of the capacitor or capacitors is initiated. If the subsequent rhythm is not determined to be ventricular fibrillation, No in Block 864, the device determines to whether to transition back to the not concerned state 302, Block 372, as described above, Block 866.

If six seconds have expired since initiation of the operating state transition delay, Yes in Block 862, meaning that the shockable or not shockable determination, Blocks 342-370 of FIG. 4, has been determined for two consecutive simultaneously sensed windows corresponding to the two sensing channels ECG 1 and ECG 2, with none of the subsequently sensed three second windows determined not to be monomorphic, indicating the rhythm continues to be monomorphic for the entire delay period, the device determines that the rhythm continues to be a monomorphic VT, and therefore the rhythm confirmation analysis is aborted and the device transitions from the concerned state 304 to the armed state 306, Block 854, where charging of the capacitor or capacitors is initiated.

Figure 13:
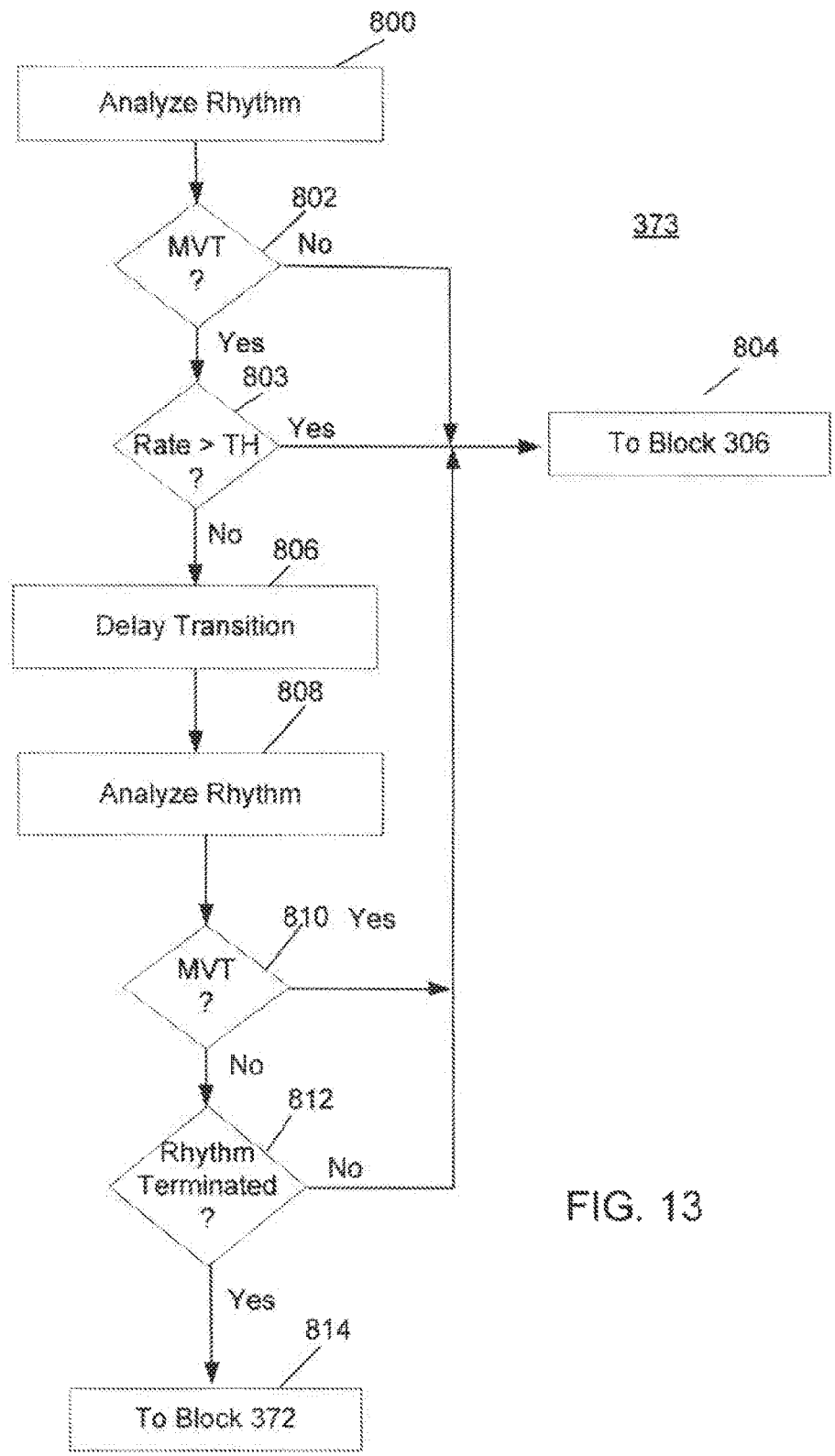
FIG. 13 is flowchart of a method for determining whether the device is to transition between operating states according to an embodiment of the present invention.

FIG. 13 is flowchart of a method for determining whether the device is to transition between operating states according to an embodiment of the present invention. FIG. 13 is similar to FIG. 8, with the exception that during the determination as to whether the rhythm is monomorphic ventricular tachycardia in Block 802, if the rhythm is determined monomorphic, Yes in Block 802, the device determines whether the rate of monomorphic ventricular tachycardia is greater than a predetermined rate threshold, Block 803. According to one embodiment, the predetermined rate threshold of Block 803 may be set to a rate between 240 and 300 beats per minute for example.

If the rate of monomorphic ventricular tachycardia is greater than a predetermined rate threshold, Yes in Block 803, the device transitions from the concerned state 304 to the armed state 306, Block 804, where charging of the capacitor or capacitors is initiated. If the rate of monomorphic ventricular tachycardia is not greater than a predetermined rate threshold, No in Block 803, the device delays transitioning from the not concerned state 304 to the concerned state, Block 806, as described above.

Thus, a method and apparatus for discriminating a cardiac event have been presented in the foregoing description with reference to specific embodiments. It is appreciated that various modifications to the referenced embodiments may be made without departing from the scope of the disclosure as set forth in the following claims.

We claim:
1. A device comprising:
at least one output capacitor; and
circuitry configured to:
obtain a cardiac signal;
perform a first analysis of a first segment of the cardiac signal;
detect a shockable ventricular cardiac event based on at least the first analysis of the first segment of the cardiac signal;
perform a second analysis of the first segment of the cardiac signal, the second analysis being different than the first analysis;
detect that the shockable ventricular cardiac event is monomorphic ventricular tachycardia (MVT) based on the second analysis; and
delay initiation of charging of the output capacitor for a threshold period of time in response to detecting that the shockable ventricular cardiac event is MVT;
detect that the shockable ventricular cardiac event is MVT after the threshold period of time;
initiate charging of the output capacitor in response to detecting that the shockable ventricular cardiac event is MVT after the threshold period of time;
cause the output capacitor to discharge to deliver shock therapy; and
decrease the threshold period of time for which charging of the output capacitor is delayed for subsequently detected MVT in response to detecting that the shockable ventricular cardiac event is MVT after the threshold period of time.
2. The device of claim 1, wherein to perform the second analysis, the circuitry is configured to:
identify a plurality of R-waves within the first segment; and
compare a morphology of a selected R-wave of the plurality of R-waves with a morphology of at least a portion of remaining R-waves of the plurality of R-waves.
3. The device of claim 2, wherein to perform the second analysis, the circuitry is configured to:
based on comparing the morphology of the selected R-wave of the plurality of R-waves with the morphology of at least the portion of the remaining R-waves of the plurality of R-waves, determine whether the shockable ventricular cardiac event is MVT or polymorphic ventricular tachycardia (PVT).
4. The device of claim 3, wherein the circuitry is further configured to:
in response to detecting that the shockable ventricular cardiac event is PVT, initiate charging of the output capacitor.
5. The device of claim 2, wherein to perform the second analysis, the circuitry is further configured to:
determine that a threshold number of the remaining R-waves of the plurality of R-waves have morphologies that match the morphology of the selected R-wave; and
detect that the shockable ventricular cardiac event is MVT in response to the threshold number of the remaining R-waves of the plurality of R-waves having morphologies that match the morphology of the selected R-wave.
6. The device of claim 1, wherein the circuitry is configured to:
detect, while delaying charging of the output capacitor, termination of the MVT shockable ventricular cardiac event; and
continue to monitor for a subsequent shockable ventricular cardiac event without initiating charging of the output capacitor for the shockable ventricular cardiac event in response to detecting termination of the shockable ventricular cardiac event.
7. The device of claim 6, wherein the circuitry is configured to increase a period of time for which charging of a output capacitor is delayed for subsequently detected MVT in response to detecting termination of the shockable ventricular cardiac event.
8. The device of claim 1, wherein the circuitry is configured to detect that the shockable ventricular cardiac event is not MVT based on the second analysis and initiate charging of the output capacitor in response to detecting that the shockable ventricular cardiac event is not MVT; and
the device further comprising control circuitry configured to discharge the output capacitor to deliver shock therapy.
9. The device of claim 1, wherein the circuitry is configured to:
while delaying charging of the output capacitor, performing the first analysis on at least one of a second segment of the cardiac signal and a third segment of a second cardiac signal, wherein the second segment and the third segment correspond with portions of the cardiac signal and the second cardiac signal that are simultaneously sensed and further wherein the second segment and the third segment are sensed after the first segment;
detect, while delaying charging of the output capacitor, continuation of the shockable ventricular cardiac event based on the first analysis of the at least one of the second segment and the third segment;

perform, while delaying charging of the output capacitor, the second analysis of the at least one of the second segment and the third segment;
continue, while delaying charging of the output capacitor, to detect that the shockable ventricular cardiac event is MVT based on the second analysis of the at least one of the second segment and the third segment;
initiate charging of the output capacitor in response to continuing to detect that the shockable ventricular cardiac event is MVT; and
discharge the output capacitor to deliver shock therapy.

10. The device of claim 1, further comprising:
a plurality of electrodes configured to sense the cardiac signal.

11. The device of claim 1, wherein the device comprises an implantable device.

12. A method comprising:
obtaining, via a plurality of electrodes, a cardiac signal;
performing, by circuitry, a first analysis of a first segment of the cardiac signal;
detecting, by the circuitry, a shockable ventricular cardiac event based on at least the first analysis of the first segment of the cardiac signal;
performing, by the circuitry, a second analysis of the first cardiac signal, the second analysis being different than the first analysis;
detecting, by the circuitry, that the shockable ventricular cardiac event is monomorphic ventricular tachycardia (MVT) based on the second analysis; and
delaying, by the circuitry, initiation of charging of a output capacitor for a threshold period of time in response to detecting that the shockable ventricular cardiac event is MVT;
detecting that the shockable ventricular cardiac event is MVT after the threshold period of time;
initiating charging of the output capacitor in response to detecting that the shockable ventricular cardiac event is MVT after the threshold period of time;
causing the output capacitor to discharge to deliver shock therapy; and
decreasing the threshold period of time for which charging of the output capacitor is delayed for subsequently detected MVT in response to detecting that the shockable ventricular cardiac event is MVT after the threshold period of time.

13. The method of claim 12, further comprising:
detecting, by the circuitry for a second segment of a second cardiac signal, that the shockable ventricular cardiac event is not MVT based on the second analysis; and
initiating, by the circuitry, charging of the output capacitor in response to detecting that the shockable ventricular cardiac event is not MVT; and
discharging the output capacitor to deliver shock therapy.

14. The method of claim 12, wherein performing the second analysis comprises:
identifying a plurality of R-waves within the first segment; and
comparing a morphology of a selected R-wave of the plurality of R-waves with a morphology of at least a portion of remaining R-waves of the plurality of R-waves.

15. A device comprising:
at least one output capacitor; and
circuitry configured to:
obtain a cardiac signal;
perform a first analysis of a first segment of the cardiac signal;
detect a shockable ventricular cardiac event based on at least the first analysis of the first segment of the cardiac signal;
perform a second analysis of the first segment of the cardiac signal, the second analysis being different than the first analysis;
detect that the shockable ventricular cardiac event is monomorphic ventricular tachycardia (MVT) based on the second analysis; and
delay initiation of charging of the output capacitor in response to detecting that the shockable ventricular cardiac event is MVT;
while delaying charging of the output capacitor, performing the first analysis on at least one of a second segment of the cardiac signal and a third segment of a second cardiac signal, wherein the second segment and the third segment correspond with portions of the cardiac signal and the second cardiac signal that are simultaneously sensed and further wherein the second segment and the third segment are sensed after the first segment;
detect, while delaying charging of the output capacitor, continuation of the shockable ventricular cardiac event based on the first analysis of the at least one of the second segment and the third segment;
perform, while delaying charging of the output capacitor, the second analysis of the at least one of the second segment and the third segment;
while delaying charging of the output capacitor, detect that the shockable ventricular cardiac event is MVT based on the second analysis of the at least one of the second segment and the third segment;
initiate charging of the output capacitor in response to continuing to detect that the shockable ventricular cardiac event is MVT; and
discharge the output capacitor to deliver shock therapy.

16. The device of claim 15, wherein the circuitry is configured to detect that the shockable ventricular cardiac event is not MVT based on the second analysis and initiate charging of the output capacitor in response to detecting that the shockable ventricular cardiac event is not MVT; and
the device further comprising control circuitry configured to discharge the output capacitor to deliver shock therapy.

17. The device of claim 15, wherein to perform the second analysis, the circuitry is configured to:
identify a plurality of R-waves within the first segment; and
compare a morphology of a selected R-wave of the plurality of R-waves with a morphology of at least a portion of remaining R-waves of the plurality of R-waves.

18. The device of claim 17, wherein to perform the second analysis, the circuitry is configured to:
based on comparing the morphology of the selected R-wave of the plurality of R-waves with the morphology of at least the portion of the remaining R-waves of the plurality of R-waves, determine whether the shockable ventricular cardiac event is MVT or polymorphic ventricular tachycardia (PVT).

19. The device of claim 18, wherein the circuitry is further configured to:
in response to detecting that the shockable ventricular cardiac event is PVT, initiate charging of the output capacitor.

20. The device of claim 17, wherein to perform the second analysis, the circuitry is further configured to:
- determine that a threshold number of the remaining R-waves of the plurality of R-waves have morphologies that match the morphology of the selected R-wave; and
- detect that the shockable ventricular cardiac event is MVT in response to the threshold number of the remaining R-waves of the plurality of R-waves having morphologies that match the morphology of the selected R-wave.

* * * * *